United States Patent
Sahin et al.

(10) Patent No.: US 10,669,322 B2
(45) Date of Patent: Jun. 2, 2020

(54) RNA MOLECULES ENCODING CYTOKINE FUSION PROTEINS AND METHODS OF USE THEREOF

(71) Applicants: BIONTECH RNA PHARMACEUTICALS GMBH, Mainz (DE); TRON TRANSLATIONALE ONKOLOGIE AN DER UNIVERSITÄTSMEDIZIN DER JOHANNES GUTENBERG-UNIVERSITÄT MAINZ GGMBH, Mainz (DE)

(72) Inventors: Ugur Sahin, Mainz (DE); Friederike Gieseke, Mainz (DE); Sebastian Kreiter, Mainz (DE); Mustafa Diken, Mainz (DE)

(73) Assignees: BIONTECH RNA PHARMACEUTICALS GMBH, Mainz (DE); TRON—TRANSLATIONALE ONKOLOGIE AN DER UNIVERSITÄTSMEDIZIN DER JOHANNES GUTENBERG-UNIVERSITÄT MAINZ GGMBH, Mainz (DE)

( * ) Notice: Subject to any disclaimer, the term of this patent is extended or adjusted under 35 U.S.C. 154(b) by 0 days.

(21) Appl. No.: 15/780,599

(22) PCT Filed: Dec. 16, 2016

(86) PCT No.: PCT/EP2016/081401
§ 371 (c)(1),
(2) Date: May 31, 2018

(87) PCT Pub. No.: WO2017/103088
PCT Pub. Date: Jun. 22, 2017

(65) Prior Publication Data
US 2018/0371042 A1 Dec. 27, 2018

(30) Foreign Application Priority Data
Dec. 17, 2015 (WO) .................. PCT/EP2015/080299

(51) Int. Cl.
| | | |
|---|---|---|
| C07K 14/54 | (2006.01) |
| C07K 14/705 | (2006.01) |
| C12N 15/62 | (2006.01) |
| C07K 14/525 | (2006.01) |
| A61K 38/00 | (2006.01) |

(52) U.S. Cl.
CPC ............ *C07K 14/54* (2013.01); *C07K 14/525* (2013.01); *C07K 14/70578* (2013.01); *C12N 15/62* (2013.01); *A61K 38/00* (2013.01); *C07K 2319/00* (2013.01)

(58) Field of Classification Search
CPC .................. C07K 14/525; C07K 14/54; C07K 14/70578; C07K 2319/00; C12N 15/62; A61K 38/00
See application file for complete search history.

(56) References Cited

FOREIGN PATENT DOCUMENTS

WO   WO 2010/010051 A1   1/2010

OTHER PUBLICATIONS

Xie B (2014). Methods Mol. Biol. 1155:215-222. (doi: 10.1007/978-1-4939-0669-7_18).*
Kermer V, et al. (Jan. 2014) Mol. Cancer Ther. 13(1):112-121. (DOI: 10.1158/1535-7163.MCT-13-0282).*
Stratagene Catalog. p. 39, 1988.*
Wajant, et al. "Tumor therapeutics by design: targeting and activation of death receptors" Cytokine Growth Factor Reviews, vol. 16, pp. 55-76 (2005).
International Search Report and Written Opinion for International Application No. PCT/EP2016/081401 dated Jun. 22, 2017, 7 pages.

* cited by examiner

*Primary Examiner* — Robert S Landsman
(74) *Attorney, Agent, or Firm* — Sheppard Mullin Richter & Hampton LLP

(57) ABSTRACT

The present invention relates to cytokine fusion proteins and to nucleic acid molecules encoding such cytokine fusion proteins. The present invention further relates to cells, non-human organisms, pharmaceutical compositions and kits comprising the cytokine fusion proteins or the nucleic acid molecules encoding them, as well as to their use as medicaments.

28 Claims, 10 Drawing Sheets
Specification includes a Sequence Listing.

SEQUENCE LISTING

```
<160> NUMBER OF SEQ ID NOS: 29

<210> SEQ ID NO 1
<211> LENGTH: 261
<212> TYPE: PRT
<213> ORGANISM: Homo sapiens

<400> SEQUENCE: 1

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140
```

```
Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 2
<211> LENGTH: 193
<212> TYPE: PRT
<213> ORGANISM: Homo sapiens

<400> SEQUENCE: 2

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 3
<211> LENGTH: 254
<212> TYPE: PRT
<213> ORGANISM: Homo sapiens

<400> SEQUENCE: 3

Met Glu Tyr Ala Ser Asp Ala Ser Leu Asp Pro Glu Ala Pro Trp Pro
```

```
            1               5                  10                 15
        Pro Ala Pro Arg Ala Arg Ala Cys Arg Val Leu Pro Trp Ala Leu Val
                        20                 25                 30

Ala Gly Leu Leu Leu Leu Leu Leu Ala Ala Cys Ala Val Phe
                    35                 40                 45

Leu Ala Cys Pro Trp Ala Val Ser Gly Ala Arg Ala Ser Pro Gly Ser
         50                  55                 60

Ala Ala Ser Pro Arg Leu Arg Glu Gly Pro Glu Leu Ser Pro Asp Asp
         65                  70                 75                 80

Pro Ala Gly Leu Leu Asp Leu Arg Gln Gly Met Phe Ala Gln Leu Val
                        85                 90                 95

Ala Gln Asn Val Leu Leu Ile Asp Gly Pro Leu Ser Trp Tyr Ser Asp
                    100                105                110

Pro Gly Leu Ala Gly Val Ser Leu Thr Gly Gly Leu Ser Tyr Lys Glu
                    115                120                125

Asp Thr Lys Glu Leu Val Val Ala Lys Ala Gly Val Tyr Tyr Val Phe
                    130                135                140

Phe Gln Leu Glu Leu Arg Arg Val Val Ala Gly Glu Gly Ser Gly Ser
        145                 150                155                160

Val Ser Leu Ala Leu His Leu Gln Pro Leu Arg Ser Ala Ala Gly Ala
                        165                170                175

Ala Ala Leu Ala Leu Thr Val Asp Leu Pro Pro Ala Ser Ser Glu Ala
                        180                185                190

Arg Asn Ser Ala Phe Gly Phe Gln Gly Arg Leu Leu His Leu Ser Ala
                        195                200                205

Gly Gln Arg Leu Gly Val His Leu His Thr Glu Ala Arg Ala Arg His
                        210                215                220

Ala Trp Gln Leu Thr Gln Gly Ala Thr Val Leu Gly Leu Phe Arg Val
        225                 230                235                240

Thr Pro Glu Ile Pro Ala Gly Leu Pro Ser Pro Arg Ser Glu
                        245                250

<210> SEQ ID NO 4
<211> LENGTH: 183
<212> TYPE: PRT
<213> ORGANISM: Homo sapiens

<400> SEQUENCE: 4

Met Glu Arg Val Gln Pro Leu Glu Glu Asn Val Gly Asn Ala Ala Arg
        1                   5                  10                 15

Pro Arg Phe Glu Arg Asn Lys Leu Leu Leu Val Ala Ser Val Ile Gln
                        20                 25                 30

Gly Leu Gly Leu Leu Leu Cys Phe Thr Tyr Ile Cys Leu His Phe Ser
                    35                 40                 45

Ala Leu Gln Val Ser His Arg Tyr Pro Arg Ile Gln Ser Ile Lys Val
         50                  55                 60

Gln Phe Thr Glu Tyr Lys Lys Glu Lys Gly Phe Ile Leu Thr Ser Gln
        65                  70                 75                 80

Lys Glu Asp Glu Ile Met Lys Val Gln Asn Asn Ser Val Ile Ile Asn
                        85                 90                 95

Cys Asp Gly Phe Tyr Leu Ile Ser Leu Lys Gly Tyr Phe Ser Gln Glu
                    100                105                110

Val Asn Ile Ser Leu His Tyr Gln Lys Asp Glu Glu Pro Leu Phe Gln
                    115                120                125
```

```
Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 5
<211> LENGTH: 452
<212> TYPE: PRT
<213> ORGANISM: Artificial Sequence
<220> FEATURE:
<223> OTHER INFORMATION: h3_CD40L

<400> SEQUENCE: 5

Gly Asp Gln Asn Pro Gln Ile Ala Ala His Val Ile Ser Glu Ala Ser
1               5                   10                  15

Ser Lys Thr Thr Ser Val Leu Gln Trp Ala Glu Lys Gly Tyr Tyr Thr
            20                  25                  30

Met Ser Asn Asn Leu Val Thr Leu Glu Asn Gly Lys Gln Leu Thr Val
        35                  40                  45

Lys Arg Gln Gly Leu Tyr Tyr Ile Tyr Ala Gln Val Thr Phe Cys Ser
50                  55                  60

Asn Arg Glu Ala Ser Ser Gln Ala Pro Phe Ile Ala Ser Leu Cys Leu
65                  70                  75                  80

Lys Ser Pro Gly Arg Phe Glu Arg Ile Leu Leu Arg Ala Ala Asn Thr
                85                  90                  95

His Ser Ser Ala Lys Pro Cys Gly Gln Gln Ser Ile His Leu Gly Gly
            100                 105                 110

Val Phe Glu Leu Gln Pro Gly Ala Ser Val Phe Val Asn Val Thr Asp
        115                 120                 125

Pro Ser Gln Val Ser His Gly Thr Gly Phe Thr Ser Phe Gly Leu Leu
130                 135                 140

Lys Leu Gly Gly Gly Ser Gly Gly Gly Asp Gln Asn Pro Gln Ile
145                 150                 155                 160

Ala Ala His Val Ile Ser Glu Ala Ser Ser Lys Thr Thr Ser Val Leu
                165                 170                 175

Gln Trp Ala Glu Lys Gly Tyr Tyr Thr Met Ser Asn Asn Leu Val Thr
            180                 185                 190

Leu Glu Asn Gly Lys Gln Leu Thr Val Lys Arg Gln Gly Leu Tyr Tyr
        195                 200                 205

Ile Tyr Ala Gln Val Thr Phe Cys Ser Asn Arg Glu Ala Ser Ser Gln
    210                 215                 220

Ala Pro Phe Ile Ala Ser Leu Cys Leu Lys Ser Pro Gly Arg Phe Glu
225                 230                 235                 240

Arg Ile Leu Leu Arg Ala Ala Asn Thr His Ser Ser Ala Lys Pro Cys
                245                 250                 255

Gly Gln Gln Ser Ile His Leu Gly Gly Val Phe Glu Leu Gln Pro Gly
            260                 265                 270

Ala Ser Val Phe Val Asn Val Thr Asp Pro Ser Gln Val Ser His Gly
        275                 280                 285

Thr Gly Phe Thr Ser Phe Gly Leu Leu Lys Leu Gly Gly Gly Ser Gly
    290                 295                 300
```

Gly Gly Gly Asp Gln Asn Pro Gln Ile Ala Ala His Val Ile Ser Glu
305                 310                 315                 320

Ala Ser Ser Lys Thr Thr Ser Val Leu Gln Trp Ala Glu Lys Gly Tyr
            325                 330                 335

Tyr Thr Met Ser Asn Asn Leu Val Thr Leu Glu Asn Gly Lys Gln Leu
            340                 345                 350

Thr Val Lys Arg Gln Gly Leu Tyr Tyr Ile Tyr Ala Gln Val Thr Phe
            355                 360                 365

Cys Ser Asn Arg Glu Ala Ser Ser Gln Ala Pro Phe Ile Ala Ser Leu
370                 375                 380

Cys Leu Lys Ser Pro Gly Arg Phe Glu Arg Ile Leu Leu Arg Ala Ala
385                 390                 395                 400

Asn Thr His Ser Ala Lys Pro Cys Gly Gln Gln Ser Ile His Leu
            405                 410                 415

Gly Gly Val Phe Glu Leu Gln Pro Gly Ala Ser Val Phe Val Asn Val
            420                 425                 430

Thr Asp Pro Ser Gln Val Ser His Gly Thr Gly Phe Thr Ser Phe Gly
            435                 440                 445

Leu Leu Lys Leu
    450

<210> SEQ ID NO 6
<211> LENGTH: 440
<212> TYPE: PRT
<213> ORGANISM: Artificial Sequence
<220> FEATURE:
<223> OTHER INFORMATION: h3_CD27L

<400> SEQUENCE: 6

Ser Leu Gly Trp Asp Val Ala Glu Leu Gln Leu Asn His Thr Gly Pro
1               5                   10                  15

Gln Gln Asp Pro Arg Leu Tyr Trp Gln Gly Gly Pro Ala Leu Gly Arg
            20                  25                  30

Ser Phe Leu His Gly Pro Glu Leu Asp Lys Gly Gln Leu Arg Ile His
        35                  40                  45

Arg Asp Gly Ile Tyr Met Val His Ile Gln Val Thr Leu Ala Ile Cys
50                  55                  60

Ser Ser Thr Thr Ala Ser Arg His His Pro Thr Thr Leu Ala Val Gly
65                  70                  75                  80

Ile Cys Ser Pro Ala Ser Arg Ser Ile Ser Leu Leu Arg Leu Ser Phe
            85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
            115                 120                 125

Asn Thr Asp Glu Thr Phe Phe Gly Val Gln Trp Val Arg Pro Gly Gly
130                 135                 140

Gly Ser Gly Gly Gly Ser Leu Gly Trp Asp Val Ala Glu Leu Gln Leu
145                 150                 155                 160

Asn His Thr Gly Pro Gln Gln Asp Pro Arg Leu Tyr Trp Gln Gly Gly
            165                 170                 175

Pro Ala Leu Gly Arg Ser Phe Leu His Gly Pro Glu Leu Asp Lys Gly
            180                 185                 190

Gln Leu Arg Ile His Arg Asp Gly Ile Tyr Met Val His Ile Gln Val
            195                 200                 205

-continued

```
Thr Leu Ala Ile Cys Ser Ser Thr Ala Ser Arg His His Pro Thr
    210                 215                 220

Thr Leu Ala Val Gly Ile Cys Ser Pro Ala Ser Arg Ser Ile Ser Leu
225                 230                 235                 240

Leu Arg Leu Ser Phe His Gln Gly Cys Thr Ile Ala Ser Gln Arg Leu
                245                 250                 255

Thr Pro Leu Ala Arg Gly Asp Thr Leu Cys Thr Asn Leu Thr Gly Thr
                260                 265                 270

Leu Leu Pro Ser Arg Asn Thr Asp Glu Thr Phe Phe Gly Val Gln Trp
            275                 280                 285

Val Arg Pro Gly Gly Gly Ser Gly Gly Gly Ser Leu Gly Trp Asp Val
    290                 295                 300

Ala Glu Leu Gln Leu Asn His Thr Gly Pro Gln Gln Asp Pro Arg Leu
305                 310                 315                 320

Tyr Trp Gln Gly Gly Pro Ala Leu Gly Arg Ser Phe Leu His Gly Pro
                325                 330                 335

Glu Leu Asp Lys Gly Gln Leu Arg Ile His Arg Asp Gly Ile Tyr Met
                340                 345                 350

Val His Ile Gln Val Thr Leu Ala Ile Cys Ser Ser Thr Thr Ala Ser
            355                 360                 365

Arg His His Pro Thr Thr Leu Ala Val Gly Ile Cys Ser Pro Ala Ser
370                 375                 380

Arg Ser Ile Ser Leu Leu Arg Leu Ser Phe His Gln Gly Cys Thr Ile
385                 390                 395                 400

Ala Ser Gln Arg Leu Thr Pro Leu Ala Arg Gly Asp Thr Leu Cys Thr
                405                 410                 415

Asn Leu Thr Gly Thr Leu Leu Pro Ser Arg Asn Thr Asp Glu Thr Phe
                420                 425                 430

Phe Gly Val Gln Trp Val Arg Pro
                435                 440

<210> SEQ ID NO 7
<211> LENGTH: 592
<212> TYPE: PRT
<213> ORGANISM: Artificial Sequence
<220> FEATURE:
<223> OTHER INFORMATION: h3_4-1BBL

<400> SEQUENCE: 7

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
                20                  25                  30

Ile Asp Gly Pro Leu Ser Trp Tyr Ser Asp Pro Gly Leu Ala Gly Val
            35                  40                  45

Ser Leu Thr Gly Gly Leu Ser Tyr Lys Glu Asp Thr Lys Glu Leu Val
50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
                100                 105                 110

Val Asp Leu Pro Pro Ala Ser Ser Glu Ala Arg Asn Ser Ala Phe Gly
            115                 120                 125
```

```
Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
                180                 185                 190

Gly Ser Gly Gly Gly Gly Ser Gly Gly Gly Ser Arg Glu Gly Pro
        195                 200                 205

Glu Leu Ser Pro Asp Asp Pro Ala Gly Leu Leu Asp Leu Arg Gln Gly
210                 215                 220

Met Phe Ala Gln Leu Val Ala Gln Asn Val Leu Leu Ile Asp Gly Pro
225                 230                 235                 240

Leu Ser Trp Tyr Ser Asp Pro Gly Leu Ala Gly Val Ser Leu Thr Gly
                245                 250                 255

Gly Leu Ser Tyr Lys Glu Asp Thr Lys Glu Leu Val Val Ala Lys Ala
                260                 265                 270

Gly Val Tyr Tyr Val Phe Phe Gln Leu Glu Leu Arg Arg Val Val Ala
                275                 280                 285

Gly Glu Gly Ser Gly Ser Val Ser Leu Ala Leu His Leu Gln Pro Leu
290                 295                 300

Arg Ser Ala Ala Gly Ala Ala Leu Ala Leu Thr Val Asp Leu Pro
305                 310                 315                 320

Pro Ala Ser Ser Glu Ala Arg Asn Ser Ala Phe Gly Phe Gln Gly Arg
                325                 330                 335

Leu Leu His Leu Ser Ala Gly Gln Arg Leu Gly Val His Leu His Thr
                340                 345                 350

Glu Ala Arg Ala Arg His Ala Trp Gln Leu Thr Gln Gly Ala Thr Val
                355                 360                 365

Leu Gly Leu Phe Arg Val Thr Pro Glu Ile Pro Ala Gly Leu Pro Ser
370                 375                 380

Pro Arg Ser Glu Gly Gly Gly Ser Gly Gly Gly Gly Ser Gly Gly
385                 390                 395                 400

Gly Gly Ser Gly Gly Gly Gly Ser Arg Glu Gly Pro Glu Leu Ser Pro
                405                 410                 415

Asp Asp Pro Ala Gly Leu Leu Asp Leu Arg Gln Gly Met Phe Ala Gln
                420                 425                 430

Leu Val Ala Gln Asn Val Leu Leu Ile Asp Gly Pro Leu Ser Trp Tyr
                435                 440                 445

Ser Asp Pro Gly Leu Ala Gly Val Ser Leu Thr Gly Gly Leu Ser Tyr
450                 455                 460

Lys Glu Asp Thr Lys Glu Leu Val Val Ala Lys Ala Gly Val Tyr Tyr
465                 470                 475                 480

Val Phe Phe Gln Leu Glu Leu Arg Arg Val Val Ala Gly Glu Gly Ser
                485                 490                 495

Gly Ser Val Ser Leu Ala Leu His Leu Gln Pro Leu Arg Ser Ala Ala
                500                 505                 510

Gly Ala Ala Ala Leu Ala Leu Thr Val Asp Leu Pro Pro Ala Ser Ser
                515                 520                 525

Glu Ala Arg Asn Ser Ala Phe Gly Phe Gln Gly Arg Leu Leu His Leu
530                 535                 540

Ser Ala Gly Gln Arg Leu Gly Val His Leu His Thr Glu Ala Arg Ala
```

```
               545                 550                 555                 560
Arg His Ala Trp Gln Leu Thr Gln Gly Ala Thr Val Leu Gly Leu Phe
                565                 570                 575
Arg Val Thr Pro Glu Ile Pro Ala Gly Leu Pro Ser Pro Arg Ser Glu
                580                 585                 590

<210> SEQ ID NO 8
<211> LENGTH: 413
<212> TYPE: PRT
<213> ORGANISM: Artificial Sequence
<220> FEATURE:
<223> OTHER INFORMATION: h3_OX40L

<400> SEQUENCE: 8

Gln Val Ser His Arg Tyr Pro Arg Ile Gln Ser Ile Lys Val Gln Phe
1               5                   10                  15
Thr Glu Tyr Lys Lys Glu Lys Gly Phe Ile Leu Thr Ser Gln Lys Glu
                20                  25                  30
Asp Glu Ile Met Lys Val Gln Asn Asn Ser Val Ile Ile Asn Cys Asp
            35                  40                  45
Gly Phe Tyr Leu Ile Ser Leu Lys Gly Tyr Phe Ser Gln Glu Val Asn
        50                  55                  60
Ile Ser Leu His Tyr Gln Lys Asp Glu Glu Pro Leu Phe Gln Leu Lys
65                  70                  75                  80
Lys Val Arg Ser Val Asn Ser Leu Met Val Ala Ser Leu Thr Tyr Lys
                85                  90                  95
Asp Lys Val Tyr Leu Asn Val Thr Thr Asp Asn Thr Ser Leu Asp Asp
            100                 105                 110
Phe His Val Asn Gly Gly Glu Leu Ile Leu Ile His Gln Asn Pro Gly
        115                 120                 125
Glu Phe Cys Val Leu Gly Gly Ser Gly Gly Gln Val Ser His
130                 135                 140
Arg Tyr Pro Arg Ile Gln Ser Ile Lys Val Gln Phe Thr Glu Tyr Lys
145                 150                 155                 160
Lys Glu Lys Gly Phe Ile Leu Thr Ser Gln Lys Glu Asp Glu Ile Met
                165                 170                 175
Lys Val Gln Asn Asn Ser Val Ile Ile Asn Cys Asp Gly Phe Tyr Leu
            180                 185                 190
Ile Ser Leu Lys Gly Tyr Phe Ser Gln Glu Val Asn Ile Ser Leu His
        195                 200                 205
Tyr Gln Lys Asp Glu Glu Pro Leu Phe Gln Leu Lys Lys Val Arg Ser
    210                 215                 220
Val Asn Ser Leu Met Val Ala Ser Leu Thr Tyr Lys Asp Lys Val Tyr
225                 230                 235                 240
Leu Asn Val Thr Thr Asp Asn Thr Ser Leu Asp Asp Phe His Val Asn
                245                 250                 255
Gly Gly Glu Leu Ile Leu Ile His Gln Asn Pro Gly Glu Phe Cys Val
            260                 265                 270
Leu Gly Gly Gly Ser Gly Gly Gln Val Ser His Arg Tyr Pro Arg
        275                 280                 285
Ile Gln Ser Ile Lys Val Gln Phe Thr Glu Tyr Lys Lys Glu Lys Gly
    290                 295                 300
Phe Ile Leu Thr Ser Gln Lys Glu Asp Glu Ile Met Lys Val Gln Asn
305                 310                 315                 320
Asn Ser Val Ile Ile Asn Cys Asp Gly Phe Tyr Leu Ile Ser Leu Lys
```

-continued

```
                325                 330                 335
Gly Tyr Phe Ser Gln Glu Val Asn Ile Ser Leu His Tyr Gln Lys Asp
                340                 345                 350
Glu Glu Pro Leu Phe Gln Leu Lys Lys Val Arg Ser Val Asn Ser Leu
            355                 360                 365
Met Val Ala Ser Leu Thr Tyr Lys Asp Lys Val Tyr Leu Asn Val Thr
        370                 375                 380
Thr Asp Asn Thr Ser Leu Asp Asp Phe His Val Asn Gly Gly Glu Leu
385                 390                 395                 400
Ile Leu Ile His Gln Asn Pro Gly Glu Phe Cys Val Leu
                405                 410

<210> SEQ ID NO 9
<211> LENGTH: 133
<212> TYPE: PRT
<213> ORGANISM: Artificial Sequence
<220> FEATURE:
<223> OTHER INFORMATION: hIL2

<400> SEQUENCE: 9

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
    130

<210> SEQ ID NO 10
<211> LENGTH: 514
<212> TYPE: PRT
<213> ORGANISM: Artificial Sequence
<220> FEATURE:
<223> OTHER INFORMATION: hscIL12 (human p40 - Elastin-Linker - human
      p35)

<400> SEQUENCE: 10

Ile Trp Glu Leu Lys Lys Asp Val Tyr Val Val Glu Leu Asp Trp Tyr
1               5                   10                  15
Pro Asp Ala Pro Gly Glu Met Val Val Leu Thr Cys Asp Thr Pro Glu
            20                  25                  30
Glu Asp Gly Ile Thr Trp Thr Leu Asp Gln Ser Ser Glu Val Leu Gly
        35                  40                  45
Ser Gly Lys Thr Leu Thr Ile Gln Val Lys Glu Phe Gly Asp Ala Gly
    50                  55                  60
Gln Tyr Thr Cys His Lys Gly Gly Glu Val Leu Ser His Ser Leu Leu
65                  70                  75                  80
```

```
Leu Leu His Lys Lys Glu Asp Gly Ile Trp Ser Thr Asp Ile Leu Lys
                85                  90                  95
Asp Gln Lys Glu Pro Lys Asn Lys Thr Phe Leu Arg Cys Glu Ala Lys
                100                 105                 110
Asn Tyr Ser Gly Arg Phe Thr Cys Trp Trp Leu Thr Thr Ile Ser Thr
                115                 120                 125
Asp Leu Thr Phe Ser Val Lys Ser Ser Arg Gly Ser Ser Asp Pro Gln
                130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
                180                 185                 190
Val His Lys Leu Lys Tyr Glu Asn Tyr Thr Ser Ser Phe Phe Ile Arg
                195                 200                 205
Asp Ile Ile Lys Pro Asp Pro Pro Lys Asn Leu Gln Leu Lys Pro Leu
                210                 215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
                245                 250                 255
Gly Lys Ser Lys Arg Glu Lys Lys Asp Arg Val Phe Thr Asp Lys Thr
                260                 265                 270
Ser Ala Thr Val Ile Cys Arg Lys Asn Ala Ser Ile Ser Val Arg Ala
                275                 280                 285
Gln Asp Arg Tyr Tyr Ser Ser Ser Trp Ser Glu Trp Ala Ser Val Pro
                290                 295                 300
Cys Ser Val Pro Gly Val Gly Val Pro Gly Val Gly Ala Arg Asn Leu
305                 310                 315                 320
Pro Val Ala Thr Pro Asp Pro Gly Met Phe Pro Cys Leu His His Ser
                325                 330                 335
Gln Asn Leu Leu Arg Ala Val Ser Asn Met Leu Gln Lys Ala Arg Gln
                340                 345                 350
Thr Leu Glu Phe Tyr Pro Cys Thr Ser Glu Glu Ile Asp His Glu Asp
                355                 360                 365
Ile Thr Lys Asp Lys Thr Ser Thr Val Glu Ala Cys Leu Pro Leu Glu
                370                 375                 380
Leu Thr Lys Asn Glu Ser Cys Leu Asn Ser Arg Glu Thr Ser Phe Ile
385                 390                 395                 400
Thr Asn Gly Ser Cys Leu Ala Ser Arg Lys Thr Ser Phe Met Met Ala
                405                 410                 415
Leu Cys Leu Ser Ser Ile Tyr Glu Asp Leu Lys Met Tyr Gln Val Glu
                420                 425                 430
Phe Lys Thr Met Asn Ala Lys Leu Leu Met Asp Pro Lys Arg Gln Ile
                435                 440                 445
Phe Leu Asp Gln Asn Met Leu Ala Val Ile Asp Glu Leu Met Gln Ala
                450                 455                 460
Leu Asn Phe Asn Ser Glu Thr Val Pro Gln Lys Ser Ser Leu Glu Glu
465                 470                 475                 480
Pro Asp Phe Tyr Lys Thr Lys Ile Lys Leu Cys Ile Leu Leu His Ala
                485                 490                 495
```

```
Phe Arg Ile Arg Ala Val Thr Ile Asp Arg Val Met Ser Tyr Leu Asn
            500                 505                 510

Ala Ser

<210> SEQ ID NO 11
<211> LENGTH: 133
<212> TYPE: PRT
<213> ORGANISM: Artificial Sequence
<220> FEATURE:
<223> OTHER INFORMATION: hIL21

<400> SEQUENCE: 11

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 12
<211> LENGTH: 434
<212> TYPE: PRT
<213> ORGANISM: Artificial Sequence
<220> FEATURE:
<223> OTHER INFORMATION: hscIL27 (human EBI3 - Elastin-Linker - human
      IL30)

<400> SEQUENCE: 12

Arg Lys Gly Pro Pro Ala Ala Leu Thr Leu Pro Arg Val Gln Cys Arg
1               5                   10                  15

Ala Ser Arg Tyr Pro Ile Ala Val Asp Cys Ser Trp Thr Leu Pro Pro
            20                  25                  30

Ala Pro Asn Ser Thr Ser Pro Val Ser Phe Ile Ala Thr Tyr Arg Leu
        35                  40                  45

Gly Met Ala Ala Arg Gly His Ser Trp Pro Cys Leu Gln Gln Thr Pro
    50                  55                  60

Thr Ser Thr Ser Cys Thr Ile Thr Asp Val Gln Leu Phe Ser Met Ala
65                  70                  75                  80

Pro Tyr Val Leu Asn Val Thr Ala Val His Pro Trp Gly Ser Ser Ser
                85                  90                  95

Ser Phe Val Pro Phe Ile Thr Glu His Ile Ile Lys Pro Asp Pro Pro
            100                 105                 110

Glu Gly Val Arg Leu Ser Pro Leu Ala Glu Arg Gln Leu Gln Val Gln
        115                 120                 125

Trp Glu Pro Pro Gly Ser Trp Pro Phe Pro Glu Ile Phe Ser Leu Lys
    130                 135                 140
```

Tyr Trp Ile Arg Tyr Lys Arg Gln Gly Ala Ala Arg Phe His Arg Val
145                 150                 155                 160

Gly Pro Ile Glu Ala Thr Ser Phe Ile Leu Arg Ala Val Arg Pro Arg
            165                 170                 175

Ala Arg Tyr Tyr Ile Gln Val Ala Ala Gln Asp Leu Thr Asp Tyr Gly
        180                 185                 190

Glu Leu Ser Asp Trp Ser Leu Pro Ala Thr Thr Met Ser Leu Gly
    195                 200                 205

Lys Val Pro Gly Val Gly Val Pro Gly Val Gly Phe Pro Arg Pro Pro
210                 215                 220

Gly Arg Pro Gln Leu Ser Leu Gln Glu Leu Arg Glu Phe Thr Val
225                 230                 235                 240

Ser Leu His Leu Ala Arg Lys Leu Leu Ala Glu Val Arg Gly Gln Ala
            245                 250                 255

His Arg Phe Ala Glu Ser His Leu Pro Gly Val Asn Leu Tyr Leu Leu
        260                 265                 270

Pro Leu Gly Glu Gln Leu Pro Asp Val Ser Leu Thr Phe Gln Ala Trp
    275                 280                 285

Arg Arg Leu Ser Asp Pro Glu Arg Leu Cys Phe Ile Ser Thr Thr Leu
290                 295                 300

Gln Pro Phe His Ala Leu Leu Gly Gly Leu Gly Thr Gln Gly Arg Trp
305                 310                 315                 320

Thr Asn Met Glu Arg Met Gln Leu Trp Ala Met Arg Leu Asp Leu Arg
            325                 330                 335

Asp Leu Gln Arg His Leu Arg Phe Gln Val Leu Ala Ala Gly Phe Asn
        340                 345                 350

Leu Pro Glu Glu Glu Glu Glu Glu Glu Glu Glu Glu Glu Glu Glu Arg
    355                 360                 365

Lys Gly Leu Leu Pro Gly Ala Leu Gly Ser Ala Leu Gln Gly Pro Ala
370                 375                 380

Gln Val Ser Trp Pro Gln Leu Leu Ser Thr Tyr Arg Leu Leu His Ser
385                 390                 395                 400

Leu Glu Leu Val Leu Ser Arg Ala Val Arg Glu Leu Leu Leu Leu Ser
            405                 410                 415

Lys Ala Gly His Ser Val Trp Pro Leu Gly Phe Pro Thr Leu Ser Pro
        420                 425                 430

Gln Pro

<210> SEQ ID NO 13
<211> LENGTH: 40
<212> TYPE: DNA
<213> ORGANISM: Artificial Sequence
<220> FEATURE:
<223> OTHER INFORMATION: hAg-Kozak

<400> SEQUENCE: 13
attcttctgg tccccacaga ctcagagaga acccgccacc                         40

<210> SEQ ID NO 14
<211> LENGTH: 84
<212> TYPE: DNA
<213> ORGANISM: Artificial Sequence
<220> FEATURE:
<223> OTHER INFORMATION: Sec

<400> SEQUENCE: 14

```
atgagagtga ccgcccccag aaccctgatc ctgctgctgt ctggcgccct ggccctgaca    60
gagacatggg ccggaagcgg atcc                                          84
```

<210> SEQ ID NO 15
<211> LENGTH: 28
<212> TYPE: PRT
<213> ORGANISM: Artificial Sequence
<220> FEATURE:
<223> OTHER INFORMATION: Sec

<400> SEQUENCE: 15

Met Arg Val Thr Ala Pro Arg Thr Leu Ile Leu Leu Ser Gly Ala
1               5                   10                  15

Leu Ala Leu Thr Glu Thr Trp Ala Gly Ser Gly Ser
            20                  25

<210> SEQ ID NO 16
<211> LENGTH: 287
<212> TYPE: DNA
<213> ORGANISM: Artificial Sequence
<220> FEATURE:
<223> OTHER INFORMATION: 2hBgUTR

<400> SEQUENCE: 16

```
ctcgagagct cgctttcttg ctgtccaatt tctattaaag gttcctttgt tccctaagtc    60
caactactaa actgggggat attatgaagg gccttgagca tctggattct gcctaataaa   120
aaacatttat tttcattgct gcgtcgagag ctcgctttct tgctgtccaa tttctattaa   180
aggttccttt gttccctaag tccaactact aaactggggg atattatgaa gggccttgag   240
catctggatt ctgcctaata aaaacatttt attttcattg ctgcgtc                287
```

<210> SEQ ID NO 17
<211> LENGTH: 134
<212> TYPE: DNA
<213> ORGANISM: Artificial Sequence
<220> FEATURE:
<223> OTHER INFORMATION: A30LA70

<400> SEQUENCE: 17

```
gagacctggt ccagagtcgc tagcaaaaaa aaaaaaaaaa aaaaaaaaaa aaaagcatat    60
gactaaaaaa aaaaaaaaaa aaaaaaaaaa aaaaaaaaaa aaaaaaaaaa aaaaaaaaaa   120
aaaaaaaaaa aaaa                                                    134
```

<210> SEQ ID NO 18
<211> LENGTH: 45
<212> TYPE: DNA
<213> ORGANISM: Artificial Sequence
<220> FEATURE:
<223> OTHER INFORMATION: Linker

<400> SEQUENCE: 18

```
ggaggcggtg gtagtggagg tggcgggtcc ggtggaggtg gaagc                   45
```

<210> SEQ ID NO 19
<211> LENGTH: 15
<212> TYPE: PRT
<213> ORGANISM: Artificial Sequence
<220> FEATURE:
<223> OTHER INFORMATION: Linker

<400> SEQUENCE: 19

Gly Gly Gly Gly Ser Gly Gly Gly Gly Ser Gly Gly Gly Gly Ser

-continued

<210> SEQ ID NO 20
<211> LENGTH: 14
<212> TYPE: PRT
<213> ORGANISM: Artificial Sequence
<220> FEATURE:
<223> OTHER INFORMATION: Linker

<400> SEQUENCE: 20

Gly Gly Gly Gly Ser Gly Gly Gly Thr Gly Gly Gly Gly Ser
1               5                   10

<210> SEQ ID NO 21
<211> LENGTH: 20
<212> TYPE: PRT
<213> ORGANISM: Artificial Sequence
<220> FEATURE:
<223> OTHER INFORMATION: Linker

<400> SEQUENCE: 21

Gly Gly Gly Gly Ser Gly Gly Gly Gly Ser Gly Gly Gly Gly Ser Gly
1               5                   10                  15

Gly Gly Gly Ser
            20

<210> SEQ ID NO 22
<211> LENGTH: 20
<212> TYPE: PRT
<213> ORGANISM: Artificial Sequence
<220> FEATURE:
<223> OTHER INFORMATION: Linker

<400> SEQUENCE: 22

Gly Gly Gly Ser Gly Gly Gly Ser Gly Gly Ser Gly Gly Gly
1               5                   10                  15

Gly Ser Leu Gln
            20

<210> SEQ ID NO 23
<211> LENGTH: 10
<212> TYPE: PRT
<213> ORGANISM: Artificial Sequence
<220> FEATURE:
<223> OTHER INFORMATION: Linker

<400> SEQUENCE: 23

Val Pro Gly Val Gly Val Pro Gly Val Gly
1               5                   10

<210> SEQ ID NO 24
<211> LENGTH: 159
<212> TYPE: PRT
<213> ORGANISM: Artificial Sequence
<220> FEATURE:
<223> OTHER INFORMATION: hIL1-alpha

<400> SEQUENCE: 24

Ser Ala Pro Phe Ser Phe Leu Ser Asn Val Lys Tyr Asn Phe Met Arg
1               5                   10                  15

Ile Ile Lys Tyr Glu Phe Ile Leu Asn Asp Ala Leu Asn Gln Ser Ile
                20                  25                  30

Ile Arg Ala Asn Asp Gln Tyr Leu Thr Ala Ala Ala Leu His Asn Leu
            35                  40                  45

```
Asp Glu Ala Val Lys Phe Asp Met Gly Ala Tyr Lys Ser Ser Lys Asp
    50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
                    85                  90                  95

Glu Ile Pro Lys Thr Ile Thr Gly Ser Glu Thr Asn Leu Leu Phe Phe
                100                 105                 110

Trp Glu Thr His Gly Thr Lys Asn Tyr Phe Thr Ser Val Ala His Pro
                115                 120                 125

Asn Leu Phe Ile Ala Thr Lys Gln Asp Tyr Trp Val Cys Leu Ala Gly
        130                 135                 140

Gly Pro Pro Ser Ile Thr Asp Phe Gln Ile Leu Glu Asn Gln Ala
145                 150                 155
```

<210> SEQ ID NO 25
<211> LENGTH: 153
<212> TYPE: PRT
<213> ORGANISM: Artificial Sequence
<220> FEATURE:
<223> OTHER INFORMATION: hIL1-beta

<400> SEQUENCE: 25

```
Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
                20                  25                  30

Gly Gln Asp Met Glu Gln Gln Val Phe Ser Met Ser Phe Val Gln
            35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
                100                 105                 110

Glu Ser Ala Gln Phe Pro Asn Trp Tyr Ile Ser Thr Ser Gln Ala Glu
                115                 120                 125

Asn Met Pro Val Phe Leu Gly Gly Thr Lys Gly Gly Gln Asp Ile Thr
        130                 135                 140

Asp Phe Thr Met Gln Phe Val Ser Ser
145                 150
```

<210> SEQ ID NO 26
<211> LENGTH: 152
<212> TYPE: PRT
<213> ORGANISM: Artificial Sequence
<220> FEATURE:
<223> OTHER INFORMATION: hIL7

<400> SEQUENCE: 26

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45
```

```
Ala Asn Lys Glu Gly Met Phe Leu Phe Arg Ala Ala Arg Lys Leu Arg
 50                  55                  60

Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
                 85                  90                  95

Lys Gly Arg Lys Pro Ala Ala Leu Gly Glu Ala Gln Pro Thr Lys Ser
             100                 105                 110

Leu Glu Glu Asn Lys Ser Leu Lys Glu Gln Lys Lys Leu Asn Asp Leu
         115                 120                 125

Cys Phe Leu Lys Arg Leu Leu Gln Glu Ile Lys Thr Cys Trp Asn Lys
130                 135                 140

Ile Leu Met Gly Thr Lys Glu His
145                 150

<210> SEQ ID NO 27
<211> LENGTH: 114
<212> TYPE: PRT
<213> ORGANISM: Artificial Sequence
<220> FEATURE:
<223> OTHER INFORMATION: hIL15

<400> SEQUENCE: 27

Asn Trp Val Asn Val Ile Ser Asp Leu Lys Lys Ile Glu Asp Leu Ile
1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
             100                 105                 110

Thr Ser

<210> SEQ ID NO 28
<211> LENGTH: 211
<212> TYPE: PRT
<213> ORGANISM: Artificial Sequence
<220> FEATURE:
<223> OTHER INFORMATION: hIL15R-alpha_IL15

<400> SEQUENCE: 28

Ile Thr Cys Pro Pro Pro Met Ser Val Glu His Ala Asp Ile Trp Val
1               5                  10                  15

Lys Ser Tyr Ser Leu Tyr Ser Arg Glu Arg Tyr Ile Cys Asn Ser Gly
                 20                  25                  30

Phe Lys Arg Lys Ala Gly Thr Ser Ser Leu Thr Glu Cys Val Leu Asn
             35                  40                  45

Lys Ala Thr Asn Val Ala His Trp Thr Thr Pro Ser Leu Lys Cys Ile
 50                  55                  60

Arg Asp Pro Ala Leu Val His Gln Arg Pro Ala Pro Pro Gly Gly Gly
 65                  70                  75                  80
```

```
Ser Gly Gly Gly Gly Ser Gly Gly Ser Gly Gly Gly Ser Leu
            85              90              95
Gln Asn Trp Val Asn Val Ile Ser Asp Leu Lys Lys Ile Glu Asp Leu
                100             105             110
Ile Gln Ser Met His Ile Asp Ala Thr Leu Tyr Thr Glu Ser Asp Val
            115             120             125
His Pro Ser Cys Lys Val Thr Ala Met Lys Cys Phe Leu Leu Glu Leu
    130             135             140
Gln Val Ile Ser Leu Glu Ser Gly Asp Ala Ser Ile His Asp Thr Val
145             150             155             160
Glu Asn Leu Ile Ile Leu Ala Asn Asn Ser Leu Ser Ser Asn Gly Asn
                165             170             175
Val Thr Glu Ser Gly Cys Lys Glu Cys Glu Glu Leu Glu Glu Lys Asn
            180             185             190
Ile Lys Glu Phe Leu Gln Ser Phe Val His Ile Val Gln Met Phe Ile
            195             200             205
Asn Thr Ser
    210

<210> SEQ ID NO 29
<211> LENGTH: 157
<212> TYPE: PRT
<213> ORGANISM: Artificial Sequence
<220> FEATURE:
<223> OTHER INFORMATION: hIL18

<400> SEQUENCE: 29

Tyr Phe Gly Lys Leu Glu Ser Lys Leu Ser Val Ile Arg Asn Leu Asn
1               5                   10                  15
Asp Gln Val Leu Phe Ile Asp Gln Gly Asn Arg Pro Leu Phe Glu Asp
                20                  25                  30
Met Thr Asp Ser Asp Cys Arg Asp Asn Ala Pro Arg Thr Ile Phe Ile
            35                  40                  45
Ile Ser Met Tyr Lys Asp Ser Gln Pro Arg Gly Met Ala Val Thr Ile
        50                  55                  60
Ser Val Lys Cys Glu Lys Ile Ser Thr Leu Ser Cys Glu Asn Lys Ile
65                  70                  75                  80
Ile Ser Phe Lys Glu Met Asn Pro Pro Asp Asn Ile Lys Asp Thr Lys
                85                  90                  95
Ser Asp Ile Ile Phe Phe Gln Arg Ser Val Pro Gly His Asp Asn Lys
            100                 105                 110
Met Gln Phe Glu Ser Ser Ser Tyr Glu Gly Tyr Phe Leu Ala Cys Glu
        115                 120                 125
Lys Glu Arg Asp Leu Phe Lys Leu Ile Leu Lys Lys Glu Asp Glu Leu
    130                 135                 140
Gly Asp Arg Ser Ile Met Phe Thr Val Gln Asn Glu Asp
145                 150                 155
```

RNA MOLECULES ENCODING CYTOKINE FUSION PROTEINS AND METHODS OF USE THEREOF

TECHNICAL FIELD OF THE INVENTION

The present invention relates to cytokine fusion proteins and to nucleic acid molecules encoding such cytokine fusion proteins. The present invention further relates to cells, non-human organisms, pharmaceutical compositions and kits comprising the cytokine fusion proteins or the nucleic acid molecules encoding them, as well as to their use as medicaments.

BACKGROUND OF THE INVENTION

Ligands of the tumor necrosis factor (TNF) superfamily have important roles in normal development processes including apoptosis, regulation of immune cell functions and other cell type-specific responses. They also play a significant role in various acquired and genetic diseases, including cancer and autoimmune diseases.

The TNF ligand superfamily is characterized by a conserved extracellular C-terminal domain referred to as TNF homology domain (THD) (Bodmer, J. L. et al. (2002), TRENDS in Biochemical Sciences, 27(1):19-26). The THDs, which share a virtually identical tertiary fold and exhibit a sequence identity between family members of approx. 20 to 30%, are responsible for receptor binding and non-covalently interact to form (homo-)trimeric complexes which are then recognized by their specific receptors. Although most ligands are synthesized as membrane-bound proteins, more specifically type II (i.e., intracellular N-terminus and extracellular C-terminus) transmembrane proteins, soluble cytokines can be generated by proteolytic cleavage of the extracellular domains comprising the THD (Bodmer, J. L. et al. (2002), TRENDS in Biochemical Sciences, 27(1):19-26).

The term "interleukin (IL)" refers to a group of cytokines with complex immunomodulatory functions, including cell proliferation, maturation, migration and adhesion. Interleukins also play an important role in immune cell differentiation and activation (Brocker, C. et al. (2010), Human Genomics, 5:30-55).

It was an object of the present invention to provide multifunctional, in particular bifunctional or dual-acting, cytokine fusion proteins of ligands of the TNF superfamily and interleukins. It was a further object of the present invention to provide nucleic acid molecules, in particular RNA molecules, encoding such cytokine fusion proteins.

SUMMARY OF THE INVENTION

In one aspect, the present invention relates to a cytokine fusion protein comprising (i) an extracellular domain or fragment or variant thereof of a ligand of the tumor necrosis factor (TNF) superfamily and (ii) an interleukin or fragment or variant thereof, wherein the extracellular domain or fragment or variant thereof of the ligand and the interleukin or fragment or variant thereof are covalently linked.

In one embodiment, the cytokine fusion protein comprises a block comprising three extracellular domains or fragments or variants thereof of the ligand which are covalently linked, wherein the block and the interleukin or fragment or variant thereof are covalently linked.

In one embodiment, the three extracellular domains or fragments or variants thereof form a homotrimer capable of binding to a receptor of the ligand.

In one embodiment, the three extracellular domains or fragments or variants thereof and/or the block and the interleukin or fragment or variant thereof are covalently linked via peptide linkers.

In one embodiment, the cytokine fusion protein comprises a molecule/structure having the general formula

  (Formula I) or

  (Formula II), wherein A comprises the extracellular domain or fragment or variant thereof of the ligand, and B comprises the interleukin or fragment or variant thereof, and
wherein L comprises a peptide linker, and
$L_A$ is, at each occurrence, independently selected from a covalent bond and a peptide linker.

In one embodiment, L further comprises a multimerization domain, preferably a dimerization domain, allowing the multimerization, preferably dimerization, of the cytokine fusion protein.

In one embodiment, the dimerization domain is selected from the group consisting of an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an Fc domain, an uteroglobin dimerization domain and functional variants of any one of the foregoing.

In one embodiment, the cytokine fusion protein is present as a multimeric, preferably dimeric, complex.

In one embodiment, the extracellular domain or fragment or variant thereof of the ligand and the interleukin or fragment or variant thereof are covalently linked via a peptide linker.

In one embodiment, the cytokine fusion protein comprises a molecule/structure having the general formula:

  (Formula III) or

  (Formula IV), wherein A comprises the extracellular domain or fragment or variant thereof of the ligand, and B comprises the interleukin or fragment or variant thereof, and
wherein L comprises a peptide linker.

In one embodiment, the cytokine fusion protein is present as a trimeric complex, wherein three extracellular domains or fragments or variants thereof of the ligand form a homotrimer capable of binding to a receptor of the ligand.

In one embodiment, the ligand is selected from the group consisting of CD40L, CD27L, 4-1BBL, OX40L, APRIL, CD30L, EDA-A1, EDA-A2, FasL, GITRL, LIGHT, LT-alpha, TL1A, TNF-alpha, TRAIL, RANKL, and TWEAK, preferably from the group consisting of CD40L, CD27L, 4-1BBL, and OX40L.

In one embodiment, the extracellular domain of CD40L comprises or consists of amino acid residues 51 to 261 or 116 to 261 of SEQ ID NO: 1, the extracellular domain of CD27L comprises or consists of amino acid residues 52 to 193 of SEQ ID NO: 2, the extracellular domain of 4-1BBL comprises or consists of amino acid residues 71 to 254 of SEQ ID NO: 3, and/or the extracellular domain of OX40L comprises or consists of amino acid residues 51 to 183 of SEQ ID NO: 4.

In one embodiment, the interleukin is selected from the group consisting of IL2, IL12, IL21, IL27, IL1-alpha, IL1-beta, IL7, IL15, IL18, IL9, IL23, IL4, IL6, IL10, IL31 and IL33.

In one embodiment, the interleukin is a heterodimeric interleukin being present as a single polypeptide.

In one embodiment, the cytokine fusion protein further comprises at least one label or tag allowing the detection and/or isolation of the cytokine fusion protein.

In one embodiment, the cytokine fusion protein further comprises one or more modifications increasing the stability of the cytokine fusion protein.

In one embodiment, the cytokine fusion protein enhances proliferation of natural killer (NK) cells and/or T cells, preferably CD8$^+$ T cells.

In another aspect, the present invention relates to a nucleic acid molecule encoding a cytokine fusion protein as defined above.

In one embodiment, the nucleic acid molecule is operatively linked to an expression control sequence.

In one embodiment, the nucleic acid molecule is contained in a vector.

In one embodiment, the nucleic acid molecule is an RNA molecule, preferably an in vitro-transcribed (IVT) RNA molecule.

In another aspect, the present invention relates to a cell transformed or transfected with a nucleic acid molecule as defined above.

In one embodiment, the cell is a prokaryotic cell.

In one embodiment, the cell is a eukaryotic cell, preferably a mammalian cell, more preferably a human cell.

In another aspect, the present invention relates to a non-human organism transformed or transfected with a nucleic acid molecule as defined above.

In another aspect, the present invention relates to a pharmaceutical composition comprising, as an active agent, a cytokine fusion protein as defined above, a nucleic acid molecule as defined above, or a cell as defined above.

In one embodiment, the pharmaceutical composition further comprises a pharmaceutically acceptable carrier and/or excipient.

In another aspect, the present invention relates to a kit comprising a cytokine fusion protein as defined above, a nucleic acid molecule as defined above, a cell as defined above or a pharmaceutical composition as defined above.

In another aspect, the present invention relates to a cytokine fusion protein as defined above, a nucleic acid molecule as defined above, a cell as defined above, or a pharmaceutical composition as defined above for use as a medicament.

In another aspect, the present invention relates to a cytokine fusion protein as defined above, a nucleic acid molecule as defined above, a cell as defined above, or a pharmaceutical composition as defined above for use in the treatment of a disease selected from the group consisting of cancer, infectious diseases, inflammatory diseases, metabolic diseases, autoimmune disorders, degenerative diseases, apoptosis-associated diseases and transplant rejections.

In another aspect, the present relates to the use of a cytokine fusion protein as defined above, a nucleic acid molecule as defined above, a cell as defined above, or a pharmaceutical composition as defined above in the manufacture of a medicament for the treatment of a disease selected from the group consisting of cancer, infectious diseases, inflammatory diseases, metabolic diseases, autoimmune disorders, degenerative diseases, apoptosis-associated diseases and transplant rejections.

In another aspect, the present relates to a method of treatment of a disease selected from the group consisting of cancer, infectious diseases, inflammatory diseases, metabolic diseases, autoimmune disorders, degenerative diseases, apoptosis-associated diseases and transplant rejections, said method comprising administering an effective amount of a cytokine fusion protein as defined above, a nucleic acid molecule as defined above, a cell as defined above, or a pharmaceutical composition as defined above to a subject in need thereof.

DETAILED DESCRIPTION OF THE INVENTION

Figure 1:
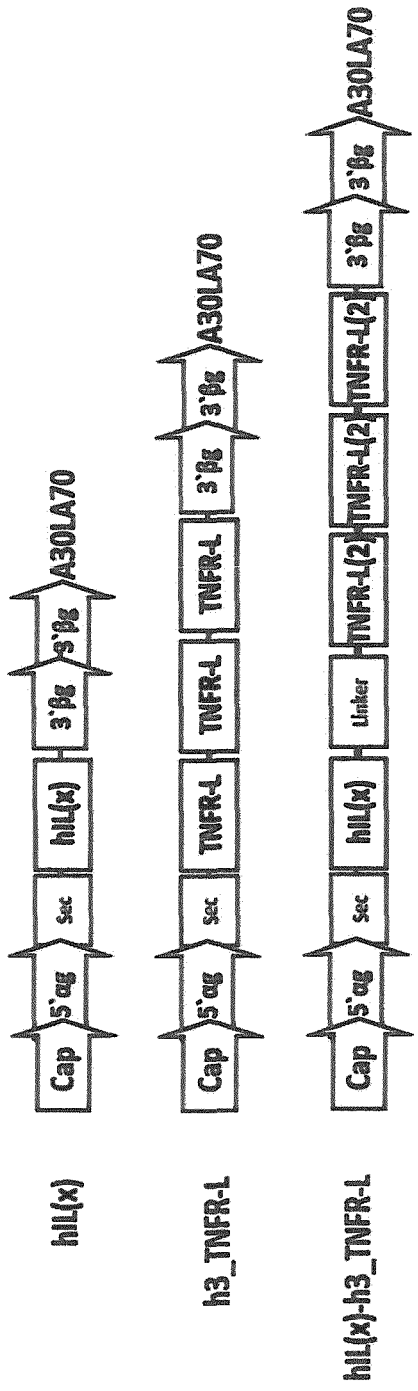
FIG. 1 shows vector design for in vitro transcription of mRNA encoding interleukins, extracellular domains of TNFR ligands and fusion proteins thereof. The plasmid constructs pST1-hAg-Kozak-sec(opt)-INSERT-2hBgUTR-A30LA70 were used as templates for in vitro transcription of RNAs encoding human interleukins (hIL(x)), TNF receptor (TNFR) ligands and fusion proteins thereof. TNFR ligands are functionally active as homotrimers—therefore, single-chain constructs were cloned, in which the inserts included three copies of the extracellular human domain separated by short linker domains (encoded amino acids: $G_3$ $SG_3$), thus coding for covalent bound trimers. These constructs are indicated as "h3_TNFR-L". To generate fusion proteins of interleukin sequences and TNFR ligands, they were connected by a linker. Constructs included a secretion signal sequence indicated as "sec".

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, certain elements of the present invention will be described. These elements may be listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995). The practice of the present invention will employ, unless otherwise indicated, conventional methods of chemistry, biochemistry, cell biology, immunology, and recombinant DNA techniques which are explained in the literature in the field (Sambrook, J. et al. (2001) Molecular Cloning: A Laboratory Manual, 3rd Ed., Cold Spring Harbor Laboratory Press, Cold Spring Harbor, N.Y.).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "cytokine" generally refers to proteins that are important in cell signaling and act through receptors. In the context of the present invention, the term particularly refers to ligands of the TNF superfamily, more particularly the extracellular domain of these ligands which forms soluble active homotrimers, as well as to interleukins.

The term "ligand of the TNF superfamily" (also referred to herein as "TNF receptor (TNFR) ligand" or "TNFR ligand" or "TNFRL" or "TNFR-L") also includes variants of a given ligand of the TNF superfamily provided these variants are functional, more particularly have an extracellular domain which is able to form a homotrimer capable of binding to a receptor of the ligand.

The term "variant of a ligand of the TNF superfamily" according to the invention, refers, in particular, to mutants, splice variants, conformation variants, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant of a ligand of the TNF superfamily" shall encompass any posttranslationally modified variants and conformation variants.

In one embodiment, the ligand of the TNF superfamily is a human ligand of the TNF superfamily. According to the present invention, the ligand of the TNF superfamily is preferably selected from the group consisting of CD40L, CD27L, 4-1BBL, OX40L, APRIL, CD30L, EDA-A1, EDA-A2, FasL, GITRL, LIGHT, LT-alpha, TL1A, TNF-alpha, TRAIL, RANKL, and TWEAK, more preferably from the group consisting of CD40L, CD27L, 4-1BBL, and OX40L.

The nucleic acid sequences and amino acid sequences of these and other ligands are known to a person skilled in the art and can be derived from public databases, such as the NCBI database, GeneCards or UniProt.

CD40 ligand (CD40L) is also known as CD154, TNFSF5, TRAP or gp39 and is a type II transmembrane glycoprotein belonging to the TNF superfamily. In one embodiment, the term CD40L, as used herein, refers to human CD40L. For example, the UniProt accession number of human CD40L is P29965. In one embodiment, CD40L has the amino acid sequence of SEQ ID NO: 1.

CD27 ligand (CD27L) is also known as CD70 or TNFSF7 and is a type II transmembrane glycoprotein belonging to the TNF superfamily. In one embodiment, the term CD27L, as used herein, refers to human CD27L. For example, the UniProt accession number of human CD27L is P32970. In one embodiment, CD27L has the amino acid sequence of SEQ ID NO: 2.

4-1BB ligand (4-1BBL) is a type II transmembrane glycoprotein belonging to the TNF superfamily and is also referred to as TNFSF9. In one embodiment, the term 4-1BBL, as used herein, refers to human 4-1BBL. For example, the UniProt accession number of human 4-1BBL is P41273. In one embodiment, 4-1BBL has the amino acid sequence of SEQ ID NO: 3.

OX40 ligand (OX40L), also known as gp34 or TNFSF4, is a type II transmembrane glycoprotein belonging to the TNF superfamily. In one embodiment, the term OX40L, as used herein, refers to human OX40L. For example, the UniProt accession number of human OX40L is P23510. In one embodiment, OX40L has the amino acid sequence of SEQ ID NO: 4.

A proliferation-inducing ligand (APRIL), also known as TALL-2, TRDL-1 or TNFSF13, is a type II transmembrane protein that is a member of the TNF superfamily. In one embodiment, the term APRIL, as used herein, refers to human APRIL. For example, the UniProt accession number of human APRIL is O75888.

CD30 ligand (CD30L), also known as TNFSF8, is a type II membrane protein belonging to the TNF superfamily. In one embodiment, the term CD30L, as used herein, refers to human CD30L. For example, the UniProt accession number of human CD30L is P32971.

Ectodysplasin-A1 (EDA-A1) is a type II transmembrane protein belonging to the TNF superfamily. It is a splice variant of Ectodysplasin-A (EDA). In one embodiment, the term EDA-A1, as used herein, refers to human EDA-A1. For example, the UniProt accession number of human EDA-A1 is Q92838-1.

Ectodysplasin-A2 (EDA-A2) is a type II transmembrane protein belonging to the TNF superfamily. It is a splice variant of Ectodysplasin-A (EDA). In one embodiment, the term EDA-A2, as used herein, refers to human EDA-A2. For example, the UniProt accession number of human EDA-A2 is Q92838-3.

Fas ligand (FasL) is also known as CD95L or TNFSF6 and is a type II transmembrane protein belonging to the TNF superfamily. In one embodiment, the term FasL, as used herein, refers to human FasL. For example, the UniProt accession number of human FasL is P48023.

GITR ligand (GITRL) is a type II transmembrane protein belonging to the TNF superfamily and has been designated TNFSF18. In one embodiment, the term GITRL, as used herein, refers to human GITRL. For example, the UniProt accession number of human GITRL is Q9UNG2.

LIGHT is also known as HVEML or TNFSF14 and is a type II transmembrane protein belonging to the TNF superfamily. In one embodiment, the term LIGHT, as used herein, refers to human LIGHT. For example, the UniProt accession number of human LIGHT is O43557.

Lymphotoxin-alpha (LT-alpha) is also known as TNF-beta or TNFSF1 and is a member of the TNF superfamily. In one embodiment, the term LT-alpha, as used herein, refers to human LT-alpha. For example, the UniProt accession number of human LT-alpha is P01374.

TL1A is a type II transmembrane protein belonging to the TNF superfamily and has been designated TNF superfamily member 15 (TNFSF15). In one embodiment, the term TL1A, as used herein, refers to human TL1A. For example, the UniProt accession number of human TL is O95150-1.

Tumor necrosis factor alpha (TNF-alpha), also known as cachectin or TNFSF2, is a type II transmembrane protein belonging to the TNF superfamily. In one embodiment, the term TNF-alpha, as used herein, refers to human TNF-alpha. For example, the UniProt accession number of human TNF-alpha is P01375.

TNF-related apoptosis-inducing ligand (TRAIL), also known as Apo-2 ligand or TNFSF10, is a type II transmembrane protein belonging to the TNF superfamily. In one embodiment, the term TRAIL, as used herein, refers to human TRAIL. For example, the UniProt accession number of human TRAIL is P50591.

Receptor activator of NF-kB (RANK) ligand (RANKL), also referred to as TRANCE, ODF, OPGL or TNFSF11, is a type II transmembrane protein belonging to the TNF superfamily. In one embodiment, the term RANKL, as used herein, refers to human RANKL. For example, the UniProt accession number of human RANKL is O14788.

TWEAK is a type II transmembrane protein belonging to the TNF superfamily and is also referred to as APO3 ligand or TNFSF12. In one embodiment, the term TWEAK, as used herein, refers to human TWEAK. For example, the UniProt accession number of human TWEAK is O43508.

The term "extracellular domain", as used herein, refers to the extracellular C-terminal part of a ligand of the TNF superfamily comprising the TNF homology domain (THD). The extracellular domain is characterized by its ability to form a (homo-)trimer capable of binding to a receptor of the ligand, and may also be referred to as "receptor-binding domain". In one embodiment, the extracellular domain of CD40L comprises or consists of amino acid residues 51 to 261 or 116 to 261, preferably 116 to 261, of SEQ ID NO: 1, the extracellular domain of CD27L comprises or consists of amino acid residues 52 to 193 of SEQ ID NO: 2, the extracellular domain of 4-1BBL comprises or consists of amino acid residues 71 to 254 of SEQ ID NO: 3, and/or the extracellular domain of OX40L comprises or consists of amino acid residues 51 to 183 of SEQ ID NO: 4.

Preferably, a "fragment or variant" of the extracellular domain which can be used in accordance with the present invention is a functional fragment or variant of the extracellular domain which, preferably, has the ability to form a (homo-)trimer capable of binding to a receptor of the ligand. Thus, such fragment or variant comprises at least a functional TNF homology domain (THD).

According to the present invention, the interleukin is preferably selected from the group consisting of IL2, IL12, IL21, IL27, IL1-alpha, IL1-beta, IL7, IL15, IL18, IL9, IL23, IL4, IL6, IL10, IL31 and IL33. In a particular embodiment, the interleukin is selected from the group consisting of IL2, IL12, IL21, IL27, IL1-alpha, IL1-beta, IL7, IL15 and IL18. In one embodiment, the interleukin is IL2. In another embodiment, the interleukin is IL12.

The nucleic acid sequences and amino acid sequences of these and other interleukins are known to a person skilled in the art and can be derived from public databases, such as the NCBI database, GeneCards or UniProt.

In one embodiment, the interleukin is a human interleukin (hIL).

For example, the UniProt accession number of human IL2 is P60568, the UniProt accession number of human IL12 is P29459 (IL12 subunit alpha, also referred to as IL12A or p35) and P29460 (IL12 subunit beta, also referred to as IL12B or p40), the UniProt accession number of human IL21 is Q9HBE4, the UniProt accession number of human IL27 is Q8NEV9 (IL27 subunit alpha, also referred to as IL27A or IL30) and Q14213 (IL27 subunit beta, also referred to as IL27B or EBI3), the UniProt accession number of human IL1-alpha is P01583, the UniProt accession number of human IL1-beta is P01584, the UniProt accession number of human IL7 is P13232, the UniProt accession number of human IL15 is P40933, the UniProt accession number of human IL18 is Q14116, the UniProt accession number of human IL9 is P15248, the UniProt accession number of human IL23 is Q9NPF7 (IL23 subunit alpha, also referred to as IL23A) and P29460 (IL12 subunit beta, also referred to as IL12B or p40), the UniProt accession number of human IL4 is P05112, the UniProt accession number of human IL6 is P05231, the UniProt accession number of human IL10 is P22301, the UniProt accession number of human IL31 is Q6EBC2, and/or the UniProt accession number of human IL33 is O95760.

In one embodiment, the interleukin is a heterodimeric interleukin. In general, the term "heterodimeric interleukin" refers to an interleukin which is formed by association of two different interleukins or interleukin subunits, which may or may not be covalently linked via one or more disulfide bridges. In one embodiment, the heterodimeric interleukin is selected from the group consisting of IL12 (formed by IL12A/p35 and IL12B/p40), IL23 (formed by IL23A and IL12B/p40) and IL27 (formed by IL27A/IL30 and IL27B/EBI3).

In one embodiment, the heterodimeric interleukin is present as a single polypeptide, e.g., in the form of a fusion protein comprising the two different interleukins or interleukin subunits forming the heterodimeric interleukin (also referred to as single-chain (sc) heterodimeric interleukin). In one embodiment, the two different interleukins or interleukin subunits are linked via a peptide linker.

Preferably, a "fragment or variant" of an interleukin which can be used in accordance with the present invention is a functional fragment or variant of the interleukin.

In one embodiment, the interleukin lacks a secretion signal sequence, in particular the natural secretion signal sequence. Means and methods for identifying the secretion signal sequence (also referred to as "signal peptide") of a given protein are known to a person skilled in the art. The secretion signal sequence of a given protein is also derivable from public databases, such as UniProt. An interleukin lacking the natural secretion signal sequence may be referred to as fragment of said interleukin. In another embodiment, the interleukin comprises the natural (or endogenous) secretion signal sequence.

Other suitable interleukin fragments in accordance with the present invention include subunits of (hetero-)dimeric interleukins, such as IL12A/p35, IL12B/p40, IL23A, IL27A/IL30 and IL27B/EBI3.

In one embodiment, the interleukin or fragment thereof comprises or consists of an amino acid sequence in accordance with one of SEQ ID NOs: 9 to 12 and 24 to 29.

The term "variant of an interleukin" according to the invention, refers, in particular, to mutants, splice variants, conformation variants, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant of an interleukin" shall encompass any post-translationally modified variants and conformation variants. It also encompasses fusion proteins comprising said interleukin.

In particular, the term "variant of an interleukin" includes natural or non-natural interleukin proteins having improved properties as compared to the respective wild-type interleukin, such as an increased stability or an increased affinity towards its receptor. Particular examples include IL2-superkine (Levin, A. M. et al. (2012), Nature, 484:529-533) and an IL15R-alpha-IL15 fusion protein (see, for example, Mortier, E. et al. (2006), J. Biol. Chem., 281(3):1612-9).

In general, the terms "part" or "fragment" are used interchangeably herein and refer to a continuous element. For example, a part of a structure, such as an amino acid sequence or protein, refers to a continuous element of said structure. A part or fragment of a protein sequence preferably comprises a sequence of at least 6, in particular at least 8, at least 12, at least 15, at least 20, at least 30, at least 50, at least 100, at least 150 or at least 200 consecutive amino acids of the protein sequence.

In general, "variants" of an amino acid sequence (e.g., that of an extracellular domain of a ligand of the TNF superfamily or that of an interleukin) comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to modifications being in positions in the amino acid sequence which are not conserved between homologous proteins or peptides and/or to replacing amino acids with other ones having similar properties. Preferably, amino acid substitutions in protein variants are conservative amino acid substitutions. A conservative amino acid substitution involves substitution of an amino acid with another one of the same family of amino acids, i.e., amino acids which are related in their side chains (e.g., in terms of the electrical charge and/or size). Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "fusion protein" generally refers to proteins created by joining two or more distinct (poly-) peptides or proteins, preferably head-to-tail (i.e., N-terminus to C-terminus or vice versa), resulting in a single protein with functional properties derived from each of the original proteins. According to the present invention, the term "cytokine fusion protein" also encompasses multimeric, e.g., dimeric or trimeric, complexes of distinct fusion proteins, which may be referred to as "subunits" of the cytokine fusion protein. Preferably, such subunits non-covalently or covalently (e.g., via disulfide bonds) associate to form the cytokine fusion protein.

A preferred subunit in accordance with the present invention has the general formula

$$\text{N'-A-L-B—C'} \hspace{2cm} \text{(Formula III) or}$$

$$\text{N'—B-L-A-C'} \hspace{2cm} \text{(Formula IV),}$$

as defined herein, wherein, preferably, three of these subunits non-covalently associate via the extracellular domains or fragments or variants thereof of the ligand to form the cytokine fusion protein.

Another preferred subunit in accordance with the present invention has the general formula

$$\text{N'-A-L}_4\text{-A-L}_4\text{-A-L-B—C'} \hspace{1cm} \text{(Formula I) or}$$

$$\text{N'—B-L-A-L}_4\text{-A-L}_4\text{-A-C'} \hspace{1cm} \text{(Formula II),}$$

as defined herein, wherein L further comprises a multimerization domain, preferably a dimerization domain, allowing the formation of a multimeric, preferably dimeric, cytokine fusion protein.

The term "block", as used herein, refers to a molecular unit/entity comprising three covalently linked extracellular domains or fragments or variants thereof of a ligand of the TNF superfamily. In one embodiment, the block has the general for A-$L_4$-A-$L_4$-A, wherein A and $L_4$ are as defined herein. In one embodiment, the block comprises or consists of an amino acid sequence in accordance with one of SEQ ID NO: 5, SEQ ID NO: 6, SEQ ID NO: 7 and SEQ ID NO: 8.

The term "covalently linked", as used herein, refers to linkage via a covalent bond or via a covalent linker molecule, such as a peptide linker.

The term "peptide linker", as used herein, refers to a peptide adapted to connect/link protein moieties, e.g., extracellular domains of a ligand of the TNF superfamily, or a block thereof and an interleukin. A peptide linker in accordance with the present invention may have any length, i.e., comprise any number of amino acid residues. However, it is preferably long enough to provide an adequate degree of flexibility to prevent the connected/linked moieties from interfering with each other's activity—e.g., the ability of the extracellular domains of a ligand of the TNF superfamily to form a homotrimer capable of binding to a receptor of the ligand, and/or the ability of such homotrimer and an interleukin fused thereto to bind to two different receptors on the same cell ("cis") or on different cells ("trans")—for example, by steric hindrance, and to allow for proper protein folding; yet it is preferably short enough to provide stability (e.g., proteolytic stability) in the cell.

In preferred embodiments, the peptide linkers have a length of 1 to 30 amino acids. Thus, according to the present invention, a peptide linker may be composed of a single amino acid residue. Preferably, a long peptide linker connects the block comprising three extracellular domains or fragments or variants thereof of the ligand of the TNF superfamily with the interleukin or fragment or variant thereof, whereas, generally, a short peptide linker is used for connecting two extracellular domains or fragments or variants thereof of the ligand. In the case of the ligand 4-1BBL, a long peptide linker may be used for connecting two of its extracellular domains or fragments or variants thereof. Short peptide linkers may consist of 12 or less such as 11, 10, 9, 8, 7, 6, 5, 4, 3, 2 or 1 amino acids, and, preferably, 1 to 7 amino acids. Long peptide linkers may consist of 12 or more, such as 12 to 30 or 12 to 25 or 12 to 20 amino acids, e.g., 15 amino acids.

The amino acids of the peptide linker may be selected from all naturally or non-naturally occurring amino acids, wherein the amino acids glycine (Gly, G), serine (Ser, S) and threonine (Thr, T) are preferred. In one embodiment, the peptide linker is a glycine-serine-threonine-rich linker or glycine-serine-rich linker, wherein at least 50%, preferably at least 60%, more preferably at least 70%, more preferably at least 80%, even more preferably at least 90% of the amino acids are a glycine or serine or threonine residue or a glycine or serine residue, respectively. In another embodiment, the amino acids are selected from glycine, serine and threonine, i.e., the peptide linker is exclusively composed of glycine, serine and threonine residues (referred to as a glycine-serine-threonine linker). In yet another embodiment, the peptide linker is exclusively composed of glycine and serine residues (referred to as a glycine-serine linker).

Preferred peptide linkers in accordance with the present invention have the general formula $(GGGGX)_n$, wherein X is, at each occurrence, independently selected from S and T, and n is an integer selected from 1 to 6, preferably 1 to 5; or a general formula selected from the group consisting of GXG, GGXGG and GGGXGGG, wherein X is S or T.

Preferred short peptide linkers have a general formula selected from the group consisting of GXG, GGXGG, GGGXGGG and GGGGXGGGG, wherein X is S or T, preferably S. A particularly preferred short peptide linker is GGGXGGG, wherein X is S or T, preferably S.

Preferred long peptide linkers have the general formula $(GGGGX)_n$, wherein X is, at each occurrence, independently selected from S an T, and n is an integer selected from 3 to 6, preferably 3 to 5, more preferably 3 and 4. Particularly preferred long peptide linkers are selected from the group consisting of $(GGGGS)_3$ (SEQ ID NO: 19), GGGGSGGGTGGGGS (SEQ ID NO: 20) and $(GGGGS)_4$ (SEQ ID NO: 21). Another preferred long linker is GGGSGGGGSGGGSGGGGSLQ (SEQ ID NO: 22).

Alternatively, an elastin or elastin-like peptide linker may be used. Preferably, said elastin or elastin-like peptide linker consists of repeats of the motif $(VPGXG)_n$, wherein X is any amino acid other than proline, and n represents the number of pentapeptide repeats. In one embodiment, n is an integer selected from 1 to 6, preferably 1 to 5.

Preferably, in case the cytokine fusion protein comprises a molecule/structure having the general formula of Formula I or II as defined herein, L comprises a long peptide linker as defined herein and/or $L_A$ is, at each occurrence, independently selected from a covalent bond (e.g., a peptide bond), a short peptide linker as defined herein and a long peptide linker as defined herein.

Preferably, in case A comprises the extracellular domain or a fragment or variant thereof of 4-1BBL, $L_A$ is, at each occurrence, independently selected from long peptide linkers as defined herein.

According to the present invention, in case the cytokine fusion protein comprises a molecule/structure having the general formula of Formula I or II as defined herein, L may further comprise a multimerization domain allowing the multimerization of the cytokine fusion protein.

In such cases, L may comprise a peptide linker as defined herein, in which the multimerization domain has been inserted. In an alternative embodiment, L may comprise two peptide linkers as defined herein sandwiching the multimerization domain, wherein the two peptide linkers may be the same or different. In one embodiment, the two peptide linkers are selected from short peptide linkers as defined herein. In yet another embodiment, the multimerization domain represents the peptide linker comprised by L.

Multimerization may occur by non-covalent interaction and/or covalent interaction, in particular via one or more disulfide bonds, between multiple (e.g., 2, 3 or 4, preferably 2 or 3, more preferably 2) multimerization domains.

Suitable multimerization domains are known to a person skilled in the art and include, for example, trimerization domains, such as a tenascin trimerization motif, a coilectin trimerization domain and streptavidin, and dimerization domains, such as an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an Fc domain, and an uteroglobin dimerization domain. In one embodiment, the multimerization domain is a dimerization domain. In one embodiment, the dimerization domain is an EHD2 domain or an MHD2 domain, e.g., as described in WO 2013/156148 A1. In one embodiment, the dimerization domain is a human EHD2 domain. Also included are functional variants of any one of the foregoing domains, e.g., domains that have been modified so as to extend their half-life and/or increase their efficiency. Suitable modifications are known to a person skilled in the art and include, but are not limited to, modifications of the Fc domain which increase its affinity for FcRn, as described, for example, in Zalevsky, J. et al. (2010), Nature Biotechnology, 28(2):157-9.

In case the cytokine fusion protein comprises a molecule/structure having the general formula of Formula III or IV as defined herein, L preferably comprises a long peptide linker as defined herein.

In one embodiment, the peptide linker linking two different interleukins or interleukin subunits forming a heterodimeric interleukin present as a single polypeptide has a length of 5 to 15 amino acids, preferably 8 to 12 amino acids. In one embodiment, the peptide linker is an elastin or elastin-like linker. In one embodiment, the peptide linker comprises or consists of the amino acid sequence VPGVGVPGVG (SEQ ID NO: 23).

The peptide linkers described herein may be replaced with non-peptidic molecules, e.g., non-peptidic oligomers and polymers (e.g., PEG molecules) of suitable lengths. Such equivalent embodiments are explicitly included in the present invention.

A "label or tag allowing the detection and/or isolation of the cytokine fusion protein" is meant to include any labels/tags known in the art for these purposes. Particularly preferred are affinity tags, such as chitin binding protein (CBP), maltose binding protein (MBP), glutathione-S-transferase (GST) and a His-tag, such as a histidine-rich sequence or poly(His) (e.g., $His_6$); solubilization tags, such as thioredoxin (TRX) and poly(NANP); chromatography tags, such as a FLAG-tag; epitope tags, such as V5-tag, myc-tag and HA-tag; and fluorescent or luminescent labels or tags, such as fluorescent proteins (e.g., GFP, YFP, RFP etc.), fluorescent dyes and luciferase. In one embodiment, the label/tag is a FLAG-tag.

The amino acid sequence of a (poly)peptide label or tag may be introduced at any position within the amino acid sequence of the cytokine fusion protein, and may, for example, take the shape of a loop within the encoded protein structure (e.g., within any of the (peptide) linkers described herein or even within the extracellular domains of the ligand or within the interleukin as long as the label/tag does not interfere with their function), or it may be N-terminally or C-terminally fused. The label or tag may further contain a cleavage site (e.g., a TEV cleavage site) that allows a removal of the label or tag from the cytokine fusion protein. Similarly, non-peptidic labels or tags, e.g., fluorescent dyes, may be conjugated to the cytokine fusion protein at any suitable site.

Cytokine fusion proteins according to the invention may also comprise an amino acid sequence for facilitating secretion of the molecule, such as an N-terminal secretion signal sequence. Preferably, the secretion signal sequence is a signal sequence that allows a sufficient passage through the secretory pathway and/or secretion into the extracellular environment. Preferably, the secretion signal sequence is cleavable and is removed from the mature cytokine fusion protein. The secretion signal sequence is preferably chosen with respect to the cell or organism which the cytokine fusion protein is produced in. In one embodiment, the secretion signal sequence comprises or consists of the amino acid sequence of SEQ ID NO: 15. In one embodiment, the secretion signal sequence is the natural (or endogenous) secretion signal sequence of one of the proteins comprised by the cytokine fusion protein, e.g., of the interleukin.

The cytokine fusion protein of the invention may further comprise a binding domain which serves, e.g., to enhance selectivity for a specific cell type. This can be achieved, e.g., by providing a binding domain that binds to a specific antigen expressed on the surface of said cell type.

The cytokine fusion protein according to the present invention may further comprise one or more modifications increasing the stability of the cytokine fusion protein. The term "stability" of the cytokine fusion protein relates to the "half-life" of the cytokine fusion protein, e.g., in vivo.

"Half-life" relates to the period of time which is needed to eliminate half of the activity, amount, or number of molecules.

The cytokine fusion protein may, for example, be conjugated to a half-life extension module. Such modules are known to a person skilled in the art and include, for example, albumin, an albumin-binding domain, Fc regions/domains of immunoglobulins, an immunoglobulin-binding domain, an FcRn-binding motif, unstructured (poly-)peptide chains, and a polymer. Particularly preferred polymers include polyethylene glycol (PEG), hydroxyethyl starch (HES), polysialic acid and hyaluronic acid.

The term "unstructured (poly-)peptide chain", as used herein, refers to a (poly-)peptide chain which lacks a fixed or ordered three-dimensional structure and is preferably hydrophilic. Unstructured (poly-)peptide chains that extend the (in vivo) half-life of peptides and proteins they are fused to are known to a person skilled in the art and include, for example, XTEN (Schellenberger, V. et al. (2009), Nat Biotechnol., 27(12):1186-90) and PAS sequences (Schlapschy, M. et al. (2013), Protein Eng Des Sel., 26(8):489-501).

The term "binding" according to the invention preferably relates to a specific binding. A binding agent, such as a cytokine fusion protein in accordance with the present invention, is specific for a predetermined target if it is capable of binding to said predetermined target while it is not capable of binding to other targets.

A "nucleic acid molecule" is according to the invention preferably deoxyribonucleic acid (DNA) or ribonucleic acid (RNA), more preferably RNA (e.g., mRNA), most preferably in vitro transcribed RNA (IVT RNA) or synthetic RNA. A nucleic acid molecule may according to the invention be in the form of a molecule which is single-stranded or double-stranded and linear or covalently closed to form a circle.

In the context of the present invention, the term "DNA" relates to a molecule which comprises deoxyribonucleotide residues and preferably is entirely or substantially composed of deoxyribonucleotide residues. "Deoxyribonucleotide" relates to a nucleotide which lacks a hydroxyl group at the 2'-position of a β-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally-occurring DNA.

In the context of the present invention, the term "RNA" relates to a molecule which comprises ribonucleotide residues and preferably is entirely or substantially composed of ribonucleotide residues. "Ribonucleotide" relates to a nucleotide with a hydroxyl group at the 2'-position of a β-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA. According to the invention, "RNA" refers to single-stranded RNA or double stranded RNA.

According to the present invention, the term "messenger RNA (mRNA)" relates to a "transcript" which may be generated by using a DNA template and may encode a peptide or protein. Typically, an mRNA comprises a 5'-untranslated region, a protein coding region, and a 3'-untranslated region. In the context of the present invention, mRNA may be generated by in vitro transcription from a DNA template. The in vitro transcription methodology is known to the skilled person. For example, there is a variety of in vitro transcription kits commercially available.

According to the invention, the RNA may be modified. For example, RNA may be stabilized by one or more modifications having stabilizing effects on RNA.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or non-naturally occurring (synthetic) ribonucleotides in order to increase its stability and/or decrease cytotoxicity and/or modulate its immunostimulating potential. For example, in one embodiment, in the RNA used according to the invention uridine is substituted partially or completely, preferably completely, by pseudouridine.

In one embodiment, the term "modification" relates to providing a RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo and/or in a cell. In one embodiment, the 5'-cap analog β-S-ARCA (D2) is used. Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be generated post-transcriptionally using capping enzymes, for example, capping enzymes of vaccinia virus.

The RNA may comprise further modifications. For example, a modification of mRNA used in the present invention may be an extension or truncation of the naturally occurring poly(A) tail.

The term "stability" of RNA relates to the "half-life" of RNA. "Half-life" relates to the period of time which is needed to eliminate half of the activity, amount, or number of molecules. In the context of the present invention, the half-life of a RNA is indicative for the stability of said RNA.

If, according to the present invention, it is desired to decrease stability of RNA, it is also possible to modify RNA so as to interfere with the function of elements as described above increasing the stability of RNA.

According to the present invention, RNA may be obtained by chemical synthesis or by in vitro transcription of an appropriate DNA template. In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". The promoter for controlling transcription can be any promoter for any RNA polymerase. Particular examples of RNA polymerases are the T7, T3, and SP6 RNA polymerases. A DNA template for in vitro transcription may be obtained by cloning of a nucleic acid, in particular cDNA, and introducing it into an appropriate vector for in vitro transcription. The cDNA may be obtained by reverse transcription of RNA. Preferably, cloning vectors are used for producing transcripts which generally are designated transcription vectors.

The term "translation" according to the invention relates to the process in the ribosomes of a cell by which a strand of messenger RNA directs the assembly of a sequence of amino acids to make a peptide or protein.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The term "expression control sequence", as used herein, is meant to refer to a nucleic acid sequence allowing the expression of the operatively linked nucleic acid molecule in a desired host cell or in an in vitro setting. Suitable expression control sequences are known to a person skilled in the art and include promoters, e.g. RNA promoters, such as a T7, T3 or SP6 promoter.

The nucleic acid molecule according to the present invention may be contained/comprised in a vector. The term "vector", as used herein, includes any vectors known to the skilled person, including plasmid vectors, cosmid vectors, phage vectors, such as lambda phage, viral vectors, such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably, said term relates according to the invention to any cell which can be transfected or transformed with an exogenous nucleic acid. Preferably, the cell when transfected or transformed with an exogenous nucleic acid and transferred to a recipient can express the nucleic acid in the recipient. The term "cell" includes prokaryotic cells, such as bacterial cells, and eukaryotic cells, such as yeast cells, fungal cells or mammalian cells. Suitable bacterial cells include cells from gram-negative bacterial strains, such as strains of *Escherichia coli*, *Proteus*, and *Pseudomonas*, and gram-positive bacterial strains, such as strains of *Bacillus*, *Streptomyces*, *Staphylococcus*, and *Lactococcus*. Suitable fungal cells include cells from the species of *Trichoderma*, *Neurospora*, and *Aspergillus*. Suitable yeast cells include cells from the species of *Saccharomyces* (for example, *Saccharomyces cerevisiae*), *Schizosaccharomyces* (for example, *Schizosaccharomyces pombe*), *Pichia* (for example, *Pichia pastoris* and *Pichia methanolica*), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR).

The term "non-human organism", as used herein, is meant to include non-human primates or other animals, in particular mammals, such as cows, horses, pigs, sheep, goats, dogs, cats, rabbits or rodents, such as mice, rats, guinea pigs and hamsters.

A pharmaceutical composition in accordance with the present invention preferably contains an effective amount of the cytokine fusion proteins, nucleic acid molecules or cells described herein (also referred to herein as "agents") to generate the desired reaction or the desired effect.

A pharmaceutical composition in accordance with the present invention is preferably sterile. Pharmaceutical compositions are usually provided in a uniform dosage form and may be prepared in a manner known per se. A pharmaceutical composition may, e.g., be in the form of a solution or suspension.

A pharmaceutical composition may further comprise one or more carriers and/or excipients, all of which are preferably pharmaceutically acceptable. The term "pharmaceutically acceptable", as used herein, refers to the non-toxicity of a material which, preferably, does not interact with the action of the active agent of the pharmaceutical composition.

The term "carrier" refers to an organic or inorganic component, of a natural or synthetic nature, in which the active component is combined in order to facilitate, enhance or enable application.

According to the invention, the term "carrier" also includes one or more compatible solid or liquid fillers, diluents or encapsulating substances, which are suitable for administration to a subject.

Possible carrier substances for parenteral administration are, e.g., sterile water, Ringer's solution, Lactated Ringer's solution, physiological saline, bacteriostatic saline (e.g., saline containing 0.9% benzyl alcohol), phosphate-buffered saline (PBS), Hank's solution, polyalkylene glycols, hydrogenated naphthalenes and, in particular, biocompatible lactide polymers, lactide/glycolide copolymers or polyoxyethylene/polyoxy-propylene copolymers.

The term "excipient", as used herein, is intended to include all substances which may be present in a pharmaceutical composition and which are not active ingredients, such as salts, binders (e.g., lactose, dextrose, sucrose, trehalose, sorbitol, mannitol), lubricants, thickeners, surface active agents, preservatives, emulsifiers, buffer substances, flavoring agents, or colorants.

Salts, which are not pharmaceutically acceptable, may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts. Salts may be added to adjust the ionic strength or tonicity.

Suitable preservatives for use in a pharmaceutical composition include antioxidants, citric acid, sodium citrate, benzalkonium chloride, chlorobutanol, cysteine, methionine, parabens and thimerosal.

Suitable buffer substances for use in a pharmaceutical composition include acetic acid in a salt, citric acid in a salt, boric acid in a salt and phosphoric acid in a salt.

The pharmaceutical composition may also be formulated as a stable lyophilized product that is reconstituted with an appropriate diluent, which, optionally, comprises one or more excipients as defined above.

The agents and compositions described herein may be administered via any conventional route, e.g., orally, pulmonary, by inhalation or parenterally, including by injection or infusion. In one embodiment, parenteral administration is used, e.g., intravenously, intraarterially, subcutaneously, intradermally or intramuscularly. The agents and compositions described herein may also be administered through sustained release administration.

Pharmaceutical compositions suitable for parenteral administration usually comprise a sterile aqueous or non-aqueous preparation of the active compound, which is preferably isotonic to the blood of the recipient. Examples of compatible carriers/solvents/diluents are sterile water, Ringer's solution, Lactated Ringer's solution, physiological saline, bacteriostatic saline (e.g., saline containing 0.9% benzyl alcohol), phosphate-buffered saline (PBS) and Hank's solution. In addition, usually sterile, fixed oils may be used as solution or suspension medium.

The agents and compositions described herein are administered in effective amounts. An "effective amount" refers to the amount, which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount of an agent or composition described herein will depend on the condition to be treated, the severeness of the disease, the individual parameters of the subject, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a subject is insufficient with an initial dose, higher doses (or effectively higher doses achieved by a different, more localized route of administration) may be used.

As used herein, the term "kit of parts (in short: kit)" refers to an article of manufacture comprising one or more containers and, optionally, a data carrier. Said one or more containers may be filled with one or more of the above mentioned means or reagents. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the cytokine fusion protein, nucleic acid molecule, cell and/or pharmaceutical composition of the present invention.

The agents and compositions described herein can be administered to a subject, e.g., in vivo, to treat or prevent a variety of disorders, such as those described herein.

According to the invention, the term "disease" refers to any pathological state, in particular cancer, infectious diseases, inflammatory diseases, metabolic diseases, autoimmune disorders, degenerative diseases, apoptosis-associated diseases and transplant rejections.

As used herein, the term "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease. The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above.

The term "cancer" according to the invention also comprises cancer metastases. By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The term "infectious disease" refers to any disease which can be transmitted from individual to individual or from organism to organism, and is caused by a microbial agent (e.g. common cold). Examples of infectious diseases include viral infectious diseases, such as AIDS (HIV), hepatitis A, B or C, herpes, herpes zoster (chicken-pox), German measles (rubella virus), yellow fever, dengue etc. flavi viruses, influenza viruses, hemorrhagic infectious diseases (Marburg or Ebola viruses), and severe acute respiratory syndrome (SARS), bacterial infectious diseases, such as Legionnaire's disease (*Legionella*), sexually transmitted diseases (e.g. chiamydia or gonorrhea), gastric ulcer (*Helicobacter*), cholera (*Vibrio*), tuberculosis, diphtheria, infections by *E. coli, Staphylococci, Salmonella* or *Streptococci* (tetanus); infections by protozoan pathogens such as malaria, sleeping sickness, leishmaniasis; toxoplasmosis, i.e. infections by Plasmodium, Trypanosoma, Leishmania and Toxoplasma; or fungal infections, which are caused, e.g., by *Cryptococcus neoformans, Histoplasma capsulatum, Coccidioides immitis, Blastomyces dermatitidis* or *Candida albicans*.

The term "inflammatory disease" refers to any disease, which is characterized by or associated with high levels of inflammation in tissues, in particular connective tissues, or degeneration of these tissues. A chronic inflammatory disease is a medical condition which is characterized by persistent inflammation. Examples of (chronic) inflammatory diseases include celiac disease, vasculitis, lupus, chronic obstructive pulmonary disease (COPD), irritable bowel disease, atherosclerosis, arthritis, ankylosing spondylitis, Crohn's disease, colitis, chronic active hepatitis, dermatitis and psoriasis.

The term "metabolic disease" refers to any disease or disorder that disrupts normal metabolism. Examples include cystinosis, diabetes, dyslipidemia, hyperthyroidism, hypothyroidism, hyperlipidemia, hypolipidemia, galactosemia, Gaucher's disease, obesity and phenylketonuria.

The term "autoimmune disorder" refers to any disease/disorder in which the body produces an immunogenic (i e immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision.

Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The term "degenerative disease" refers to any disease in which the function or structure of the affected tissues or organs will increasingly deteriorate over time. Examples include Alzheimer's disease, Parkinson's disease, amyotrophic lateral sclerosis (ALS), Huntington's disease, macular degeneration, multiple sclerosis, muscular dystrophy, Niemann Pick disease, osteoporosis and rheumatoid arthritis.

The term "apoptosis-associated diseases" refers to any disease in which alterations of apoptosis are involved. Examples include cancer, neurological disorders, such as Alzheimer's disease, Parkinson's disease, Huntington's disease, amyotrophic lateral sclerosis (ALS) and stroke, heart diseases, such as ischemia reperfusion and chronic heart failure, infectious diseases and autoimmune diseases.

The term "transplant rejection" refers to the rejection of a transplanted tissue or organ by the recipient's immune system, which may, ultimately, destroy the transplanted tissue or organ.

The term "medicament", as used herein, refers to a substance/composition used in therapy, i.e., in the treatment of a disease.

By "treat" is meant to administer a compound or composition or a combination of compounds or compositions to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

The term "subject" means according to the invention a subject for treatment, in particular a diseased subject (also referred to as "patient"), including human beings, non-human primates or other animals, in particular mammals, such as cows, horses, pigs, sheep, goats, dogs, cats, rabbits or rodents, such as mice, rats, guinea pigs and hamsters. In one embodiment, the subject/patient is a human being.

EXAMPLES

Example 1: Vector Design, Cloning and Production of In Vitro Transcribed RNA (IVT-RNA)—mRNA Encoded Cytokine Fusion Proteins Plasmid constructs (pST1-hAg-Kozak-sec-2hBgUTR-A30LA70), which were used as templates for in vitro transcription of RNAs encoding interleukins, tumor necrosis factor receptor (TNFR) ligands and fusion proteins thereof, were based on pST1-2hBgUTR-A120 (Holtkamp S. et al. (2006), Blood, 108(13):4009-17). The plasmid backbone was derived from pCMV-Script (Stratagene, La Jolla/Calif., USA) by introducing a T7 promotor, the 5'-human alpha-globulin UTR, the Kozak sequence, a 78-bp signal peptide derived from an MHC class I molecule (Sec; secretion signal sequence), two copies of the human 3'-beta-globulin UTR, the A30LA70 poly(A)-tail (L: linker sequence) and the kanamycin resistance gene. Inserts encoding for interleukins, TNFR ligands or fusion proteins thereof were introduced by cold fusion reactions with PCR products (Cold fusion kit, Biocat). DNA sequences of the relevant protein encoding section are listed in Table 1.

TABLE 1

DNA/amino acid sequences of particular sections of pST1-hAg-Kozak-sec-INSERT-2hBgUTR-A30LA70 and other plasmids used in accordance with the present invention.

| Backbone | DNA or amino acid sequences |
|---|---|
| hAg-Kozak | ATTCTTCTGGTCCCCACAGACTCAGAGAGAACCCGCCACC (SEQ ID NO: 13) |
| Sec | ATGAGAGTGACCGCCCCCAGAACCCTGATCCTGCTGCTGTCTGGCGCCCTGGCCCTGACAGAGACAT GGGCCGGAAGCGGATCC (SEQ ID NO: 14)<br>(M R V T A P R T L I L L L S G A L A L T E T W A G S G S; SEQ ID NO: 15) |
| 2hBgUTR | CTCGAGAGCTCGCTTTCTTGCTGTCCAATTTCTATTAAAGGTTCCTTTGTTCCCTAAGTCCAACTACTAA ACTGGGGGATATTATGAAGGGCCTTGAGCATCTGGATTCTGCCTAATAAAAAACATTTATTTTCATTGC TGCGTCGAGAGCTCGCTTTCTTGCTGTCCAATTTCTATTAAAGGTTCCTTTGTTCCCTAAGTCCAACTAC TAAACTGGGGGATATLATGAAGGGCCTTGAGCATCTGGATTCTGCCTAATAAAAAACATTTATTTTCAT TGCTGCGTC (SEQ ID NO: 16) |
| A30LA70 | GAGACCTGGTCCAGAGTCGCTAGCAAAAAAAAAAAAAAAAAAAAAAAAAAAAAAAAGCATATGACTAA AAAAAAAAAAAAAAAAAAAAAAAAAAAAAAAAAAAAAAAAAAAAAAAAAAAAAAAAAAAAAAAAAAA AAA (SEQ ID NO: 17) |
| (G4S)3-Linker | GGAGGCGGTGGTAGTGGAGGTGGCGGGTCCGGTGGAGGTGGAAGC (SEQ ID NO: 18)<br>(G G G G S G G G G S G G G G S; SEQ ID NO: 19) |

An optimized secretion signal sequence (sec) was cloned in front of the coding sequences in all constructs; coding sequences of human interleukins were introduced without the natural secretion signal sequence. Coding sequences for trimeric human TNFR ligands (CD40L, CD27L, OX40L and 4-1BBL) were introduced as follows: three copies of the extracellular sequence of the indicated human TNFR ligand connected in line and separated by a GS-linker; such an human insert is specified as h3_TNFR-L (h3_CD40L, h3_CD27L, h3_OX40L or h3_41BBL). To get coding sequences for interleukin TNFR ligand fusion proteins, interleukin sequences and h3_TNFR-L sequences were connected by a 15-amino acid linker ((G4S)3-Linker), respectively (Table 1 and FIG. 1). RNA-transcripts are indicated as hIL(x)-h3_TNFR-L or h3_TNFR-L-hIL(x), respectively. Protein sequences of the single h3_TNFR-Ls and single interleukins are listed in Table 2 and Table 3.

TABLE 2

Amino acid sequences of the variable inserts of pST1-hAg-Kozak-sec-INSERT-2hBgUTR-A30LA70 and plasmids encoding the extracellular domains of TNFR ligands (linker sequences are underlined).

| Insert | related amino acid of full length protein | Amino acid sequences |
|---|---|---|
| h3_CD40L | aa 116-261 | GDQNPQIAAHVISEASSKTTSVIQWAEKGYYTMSNNLVTLENGKQLTVKRQ GLYYIYAQVTFCSNREASSQAPFIASLCLKSPGRFERILLRAANTHSSAKPCGQ QSIHLGGVFELQPGASVFVNVTDPSQVSHGTGFTSFGLLKLGGGSGGGGDQ NPQIAAHVISEASSKTTSVLQWAEKGYYTMSNNLVTLENGKQLTVKRQGLYY IYAQVTFCSNREASSQAPFIASLCLKSPGRFERILLRAANTHSSAKPCGQQSIH LGGVFELQPGASVFVNVTDPSQVSHGTGFTSFGLLKLGGGSGGGGDQNPQI AAHVISEASSKTTSVLQWAEKGYYTMSNNLVTLENGKQLTVKRQGLYYIYAQ VTFCSNREASSQAPFIASLCLKSPGRFERILLRAANTHSSAKPCGQQSIHLGG VFELQPGASVFVNVTDPSQVSHGTGFTSFGLLKL (SEQ ID NO: 5) |
| h3_CD27L | aa 52-193 | SLGWDVAELQLNHTGPQQDPRLYWQGGPALGRSFLHGPELDKGQLRIHRD GIYMVHIQVTLAICSSTTASRHHPTTLAVGICSPASRSISLLRLSFHQGCTIAS QRLTPLARGDTLCTNLTGTLLPSRNTDETFFGVQWVRPGGGSGGGSLGWDV AELQLNHTGPQQDPRLYWQGGPALGRSFLHGPELDKGQLRIHRDGIYMVHI QVTLAICSSTTASRHHPTTLAVGICSPASRSISLLRLSFHQGCTIASQRLTPLA RGDTLCTNLTGTLLPSRNTDETFFGVQWVRPGGGSGGGSLGWDVAELQLN HTGPQQDPRLYWQGGPALGRSFLHGPELDKGQLRIHRDGIYMVHIQVTLAI CSSTTASRHHPTTLAVGICSPASRSISLLRLSFHQGCTIASQRLTPLARGDTLC TNLTGTLLPSRNTDETFFGVQWVRP (SEQ ID NO: 6) |
| h3_4-1BBL | aa 71-254 | REGPELSPDDPAGLLDLRQGMFAQLVAQNVLLIDGPLSWYSDPGLAGVSLT GGLSYKEDTKELVVAKAGVYYVFFQLELRRVVAGEGSGSVSLALHLQPLRSA AGAAALALTVDLPPASSEARNSAFGFQGRLLHLSAGQRLGVHLHTEARARH AWQLTCLGATVLGLFRVTPEIPAGLPSPRSEGGGGSGGGGSGGGGSGGGGS REGPELSPDDPAGLLDLRQGMFAQLVAQNVLLIDGPLSWYSDPGLAGVSLT GGLSYKEDTKELVVAKAGVYYVFFQLELRRVVAGEGSGSVSLALHLQPLRSA AGAAALALTVDLPPASSEARNSAFGFQGRLLHLSAGQRLGVHLHTEARARH AWQLTQGATVLGLFRVTPEIPAGLPSPRSEGGGGSGGGGSGGGGSGGGGS REGPELSPDDPAGLLDLRQGMFAQLVAQNVLLIDGPLSWYSDPGLAGVSLT GGLSYKEDTKELVVAKAGVYYVFFQLELRRVVAGEGSGSVSLALHLQPLRSA AGAAALALTVDLPPASSEARNSAFGFQGRLLHLSAGQRLGVHLHTEARARH AWQLTQGATVLGLFRVTPEIPAGLPSPRSE (SEQ ID NO: 7) |
| h3_OX40L | aa 51-183 | QVSHRYPRIQSIKVQFTEYKKEKGFILTSQKEDEIMKVQNNSVIINCDGFYLIS LKGYFSQEVNISLHYQKDEEPLFQLKKVRSVNSLMVASLTYKDKVYLNVTTD NTSLDDFHVNGGELILIHQNPGEFCVLGGGSGGGQVSHRYPRIQSIKVQFTE YKKEKGFILTSQKEDEIMKVQNNSVIINCDGFYLISLKGYFSQEVNISLHYQKD EEPLFQLKKVRSVNSLMVASLTYKDKVYLNVTTDNTSLDDFHVNGGELILIHQ NPGEFCVLGGGSGGGQVSHRYPRIQSIKVQFTEYKKEKGFILTSQKEDEIMK VQNNSVIINCDGFYLISLKGYFSQEVNISLHYQKDEEPLFQLKKVRSVNSLMV ASLTYKDKVYLNVTTDNTSLDDFHVNGGELILIHQNPGEFCVL (SEQ ID NO: 8) |

TABLE 3

Amino acid sequences of the variable inserts of pST1-hAg-Kozak-sec-INSERT-2hBgUTR-A30LA70 and plasmids encoding interleukins (linker sequences are underlined).

| Insert | related amino acid of full length protein | Amino acid sequences |
|---|---|---|
| hIL2 | aa 21-153 | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETT FMCEYADETATIVEFLNRWITFCQSIISTLT (SEQ ID NO: 9) |
| hscIL12 (human p40-Elastin-Linker-human p35) | p40: aa 23-328; p35: aa 23-219 | IWELKKDVYVVELDWYPDAPGEMVVLTCDTPEEDGITWTLDQSSEVLGS GKTLTIQVKEFGDAGQYTCHKGGEVLSHSLLLLHKKEDGIWSTDILKDQK EPKNKTFLRCEAKNYSGRFTCWWLTTISTDLTFSVKSSRGSSDPQGVTCG AATLSAERVRGDNKEYEYSVECQEDSACPAAEESLPIEVMVDAVHKLKYE NYTSSFFIRDIIKPDPPKNLQLKPLKNSRQVEVSWEYPDTWSTPHSYFSLT FCVQVQGKSKREKKDRVFTDKTSATVICRKNASISVRAQDRYYSSSWSE WASVPCSVPGVGVPGVGARNLPVATPDPGMFPCLHHSQNLLRAVSNML QKARQTLEFYPCTSEEIDHEDITKDKTSVEACLPLELTKNESCLNSRETSF ITNGSCLASRKTSFMMALCLSSIYEDLKMYQVEFKTMNAKLLMDPKRQIF LDQNMLAVIDELMQALNFNSETVPQKSSLEEPDFYKTKIKLCILLHAFRIR AVTIDRVMSYLNAS (SEQ ID NO: 10) |

TABLE 3-continued

Amino acid sequences of the variable inserts of pST1-hAg-Kozak-sec-INSERT-2hBgUTR-A30LA70 and plasmids encoding interleukins (linker sequences are underlined).

| Insert | related amino acid of full length protein | Amino acid sequences |
|---|---|---|
| hIL21 | aa 23-155 | QGQDRHMIRMRQLIDIVDQLKNYVNDLVPEFLPAPEDVETNCEWSAFSC FQKAQLKSANTGNNERIINVSIKKLKRKPPSTNAGRRQKHRLTCPSCDSY EKKPPKEFLERFKSLLQKMIHQLSSRTHGSEDS (SEQ ID NO: 11) |
| hscIL27 (human EBI3-Elastin-Linker-human IL30) | EBI3: aa 21-229; IL30: aa 29-243 | RKGPPAALTLPRVQCRASRYPIAVDCSWTLPPAPNSTSPVSFIATYRLGM AARGHSWPCLQQTPTSTSCTITDVQLFSMAPYVLNVTAVHPWGSSSSFV PFITEHIIKPDPPEGVRLSPLAERQLQVQWEPPGSWPFPEIFSLKYWIRYK RQGAARFHRVGPIEATSFILRAVRPRARYYIQVAAQDLTDYGELSDWSLP ATATMSLGK<u>VPGVGVPGVG</u>FPRPPGRPQLSLQELRREFTVSLHLARKLLA EVRGQAHRFAESHLPGVNLYLLPLGEQLPDVSLTFQAWRRLSDPERLCFI STTLQPFHALLGGLGTQGRWTNMERMQLWAMRLDLRDLQRHLRFQVL AAGFNLPEEEEEEEEEEEERKGLLPGALGSALQGPAQVSWPQLLSTYRL LHSLELVLSRAVRELLLLSKAGHSVWPLGFPTLSPQP (SEQ ID NO: 12) |
| hIL1-aplpha | aa 113-271 | SPFSFLSNVKYNFMRIIKYEFILNDALNQSIIRANNDQYLTAAALHNLDEA VKFDMGAYKSSKDDAKITVILRISKTQLYVTAQDEDQPVLLKEMPEIPKTI TGSETNLLFFWETHGTKNYFTSVAHPNLFIATKQDYWVCLAGGPPSITDF QILENQA (SEQ ID NO: 24) |
| hIL1-beta | aa 117-269 | APVRSLNCTLRDSQQKSLVMSGPYELKALHLQGQDMEQQVVFSMSFVQ GEESNDKIPVALGLKEKNLYLSCVLKDDKPTLQLESVDPKNYPKKKMEKR FVFNKIEINNKLEFESAQFPNWYISTSQAENMPVFLGGTKGGQDITDFT MQFVSS (SEQ ID NO: 25) |
| hIL7 | aa 26-117 | DCDIEGKDGKQYESVLMVSIDQLLDSMKEIGSNCLNNEFNFFKRHICDAN KEGMFLFRAARKLRQFLKMNSTGDFDLHLLKVSEGTTILLNCTGQVKGRK PAALGEAQPTKSLEENKSLKEQKKLNDLCFLKRLLQEIKTCWNKILMGTK EH (SEQ ID NO: 26) |
| hIL15 | aa 49-162 | NWVNVISDLKKIEDLIQSMHIDATLYTESDVHPSCKVTAMKCFLLELQVIS LESGDASIHDTVENLIILANNSLSSNGNVTESGCKECEELEEKNIKEFLQSF VHIVQMFINTS (SEQ ID NO: 27) |
| hIL15R-alpha_IL15 | hIL15R-alpha: Q13261[31-107]; IL15: aa 49-162 | ITCPPPMSVEHADIWVKSYSLYSRERYICNSGFKRKAGTSSLTECVLNKAT NVAHWTTPSLKCIRDPALVHQRPAPP<u>GGGSGGGGSGGGSGGGGSLQN</u> WVNVISDLKKIEDLIQSMHIDATLYTESDVHPSCKVTAMKCFLLELQVISL ESGDASIHDTVENLIILANNSLSSNGNVTESGCKECEELEEKNIKEFLQSF VHIVQMFINTS (SEQ ID NO: 28) |
| hIL18 | aa 37-193 | YFGKLESKLSVIRNLNDQVLFIDOGNRPLFEDMTDSDCRDNAPRTIFIISM YKDSQPRGMAVTISVKCEKISTLSCENKIISFKEMNPPDNIKDTKSDIIFFQ RSVPGHDNKMQFESSSYEGYFLACEKERDLFKLILKKEDELGDRSIMFTV QNED (SEQ ID NO: 29) |

For generation of IVT-RNAs, plasmids were linearized downstream of the poly(A) tail using a class II restriction endonuclease. Linearized plasmids were purified by magnetic beads (Dynabeads® MyOne™ Carboxylic Acid; Invitrogen), quantified spectrophotometrically, and subjected to in vitro transcription with T7 RNA polymerase (Thermo Scientific) according to the manufacturer's instructions. Additionally, the cap analog f3-S-ARCA (D2) was incorporated and finally the RNA was purified using MEGA Kit (Ambion).

Example 2: Intracellular Expression of Interleukin TNFR Ligand Fusion Proteins After IVT-RNA Electroporation In order to check expression of fusion proteins, corresponding IVT-RNA was electroporated into K562 cells. K562, a human cell line derived from chronic myeloid leukemia (obtained from ATCC, Manassas, Va., USA), was cultivated in RPMI 1640 GlutaMAX supplemented with 5% FCS (both life technologies), 100 IU/mL penicillin, and 100 µg/mL streptomycin (life technologies). For electroporation of K562 in a 96-well plate system, harvested cells were washed once in X-Vivo15 medium (Lonza) and re-suspended to a final concentration of 500.000 cells/150 µl in X-Vivo15 again. 150 µl of cell suspension were pipetted into each well of a 96-well plate already containing the required IVT-RNAs for multi-well-electroporation (Biorad). After mixing, electroporation was performed in the Gene Pulser MXcell electroporation system from Biorad (250 V, 1×30 ms pulse), the 96-well electroporation device. Immediately after electroporation, cells were transferred into a new culture plate containing fresh medium without antibiotics and rested for about 6 hours in the incubator. For intracellular staining of K562, cells were then incubated with GolgiPlug and GolgiStop (BD Biosciences, San Jose, Calif.) for 16 hours according to the manufacturer's protocol. On the next day, cells were washed with PBS and fixed for 20 min in BD Cytofix Buffer (BD Biosciences) at room temperature. After that, cells were washed again in PBS and permeabilized by washing and transferring the cells into 1× Penn/Wash Buffer (BD Biosciences). After 10 min of incubation, cells were stained with anti-interleukin antibodies and anti-CD40 antibody diluted in 1× Perm/Wash Buffer for 30 min at room temperature in the dark, followed by 3 washing steps with 1× Perm/Wash Buffer. Cells were then directly analyzed by flow cytometry using a FACS Canto II flow cytometer (BD Biosciences). Analysis was performed using the FlowJo software (Tree Star, Ashland, Oreg., USA).

Figure 2:
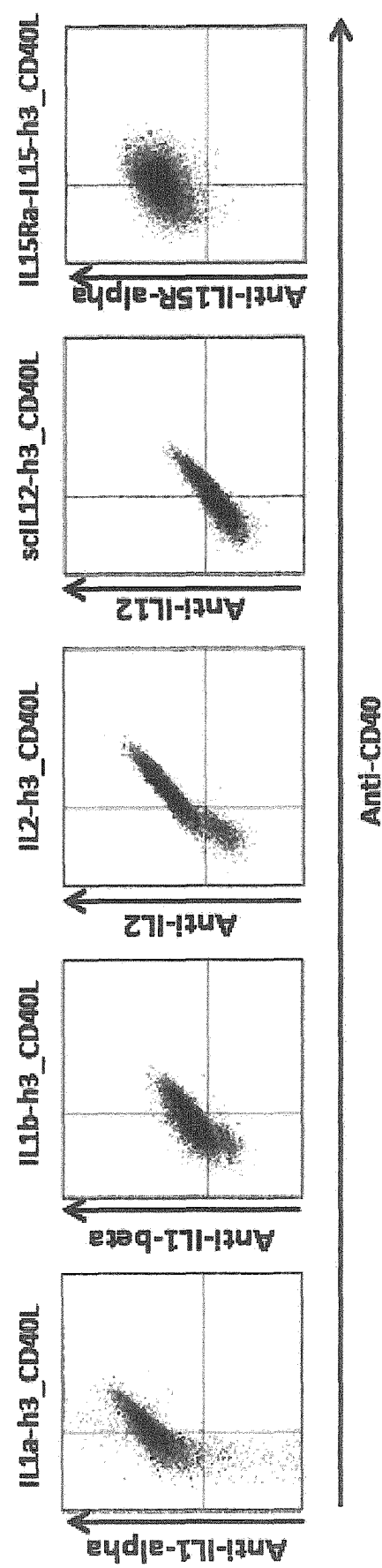
FIG. 2 shows intracellular expression of fusion proteins after IVT-RNA electroporation. K562 cells were electroporated with IVT-RNA encoding interleukin TNFR ligand fusion proteins. 6 hours after electroporation, protein export was blocked with GolgiPlug and GolgiSTOP and after 12 hours of incubation, cells were stained intracellularly for interleukins as indicated and for CD40L, respectively.

Electroporation of mRNA encoding fusion proteins of interleukins with TNFR ligands resulted in intracellular protein expression, which was detectable by intracellular antibody staining. FIG. 2 shows examples of hIL(x)-h3_CD40L fusions constructs: both the interleukin-part and CD40L-part were detected by the corresponding antibodies.

Figure 3:
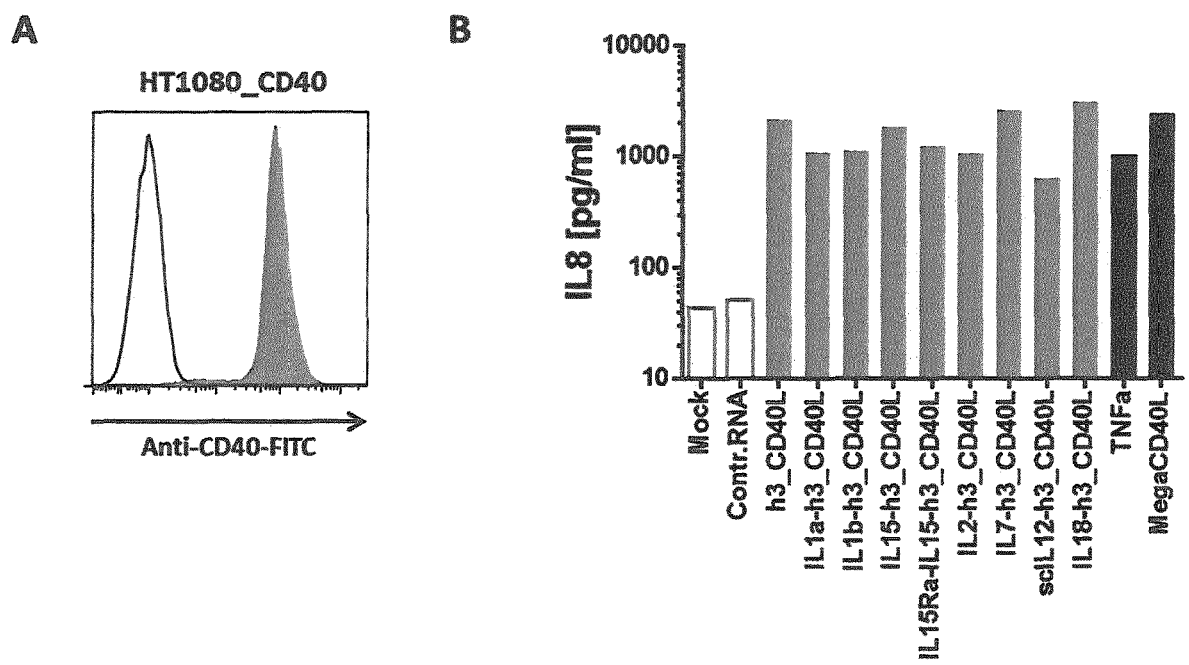
FIG. 3 shows receptor activation properties of proteins expressed upon electroporation of IVT-RNA encoding interleukin CD40L fusion constructs. (A) Stabile human CD40 transfectants of HT1080 were stained with anti-CD40-FITC. (B) IL-8 release due to activation of HT1080_hCD40 upon incubation with supernatants from K562 electroporated with IVT-RNA encoding indicated h3_CD40L fusion protein. h3_CD40L single proteins and the fusion proteins resulted in IL-8-secretion upon electroporation of the corresponding RNA (7.5 µg RNA per electroporation). Recombinant protein MegaCD40L (Enzo life sciences) and recombinant TNF-alpha induced IL8-secretion to comparable amounts.

Example 3: Receptor Activation Properties of Proteins Expressed Upon Electroporation of IVT-RNA Encoding Interleukin CD40L Fusion Constructs In order to check protein functions of fusion proteins, a reporter assay measuring CD40 activation by its ligand was performed using HT1080_CD40 cells, which were cultivated in RPMI 1640 GlutaMAX supplemented with 5% FCS, 100 IU/mL penicillin, and 100 µg/mL streptomycin. Cell surface expressions of TNF receptors on HT1080-transfectants were analyzed by FACS. To that end, HT0180_CD40 were stained using anti-human CD40-FITC antibody (Biolegend) (FIG. 3 A). Human interleukin TNFR ligand fusion proteins were produced by electroporation of K562 as described above (see Example 2) Immediately after electroporation, cells were transferred into a new culture plate by adding 100 µl of fresh medium and rested for about 3 hours in the incubator. Then, cells were centrifuged and cell pellets were re-suspended in 500 µl RPMI 1640 GlutaMAX with 0.5% FCS for overnight incubation (about 16 hours). On the next day, 100 µl of supernatants containing the secreted fusion proteins were transferred to confluent layers of HT1080_CD40 transfectants. CD40 receptor activation results in NF-kappaB pathway activation following IL-8 release by HT1080_CD40 cells. After 6-8 hours of incubation, cell-free supernatants were collected and IL8-concentrations were measured by an IL-8 ELISA kit (Biolegend) according to the manufacturer's protocol.

Activation of CD40 receptor on HT1080_CD40 was detected upon electroporation of all tested h3_CD40L fusion proteins in comparable extent as recombinant CD40 (MegaCD40L, enzo life sciences) and as recombinant TNF-alpha, which activates cells independently of CD40-receptor. Application of single h3_CD40L constructs and h3_CD40L fusion constructs resulted in comparable activation confirming functionality of CD40L within the fusion protein (FIG. 3B).

Example 4: Effects of IVT-RNA Encoded hIL2-h3_TNFR Ligand Fusion Proteins on T Cell and NK Cell Proliferation In order to analyze effects mediated by interleukin TNFR ligand fusion constructs (IVT-RNA) on peripheral blood mononuclear cells (PBMCs), a CFSE proliferation assay was performed. K562 cells were used for production of interleukin TNFR ligand fusion proteins. To that end, K562 were electroporated in a 96-well plate-system. Cells were washed once in X-Vivo15 medium and re-suspended to 500.000 cells/150 µl in X-Vivo15 again. 150 µl of cell suspension were pipetted into the 96-well plate already containing the required IVT-RNAs (20 pmol/well referring to the corresponding translated protein) for multi-well-electroporation. After mixing, electroporation was performed in the Gene Pulser MXcell electroporation system (250 V, 1×30 ms pulse). Immediately after electroporation, cells were transferred into a new culture plate by adding 100 of fresh medium and rested for about 1-3 hours in the incubator. Then, cells were centrifuged and cell pellets were re-suspended in 500 µl RPMI 1640 GlutaMAX with 0.5% FCS for incubation for 24 hours.

Figure 4A:
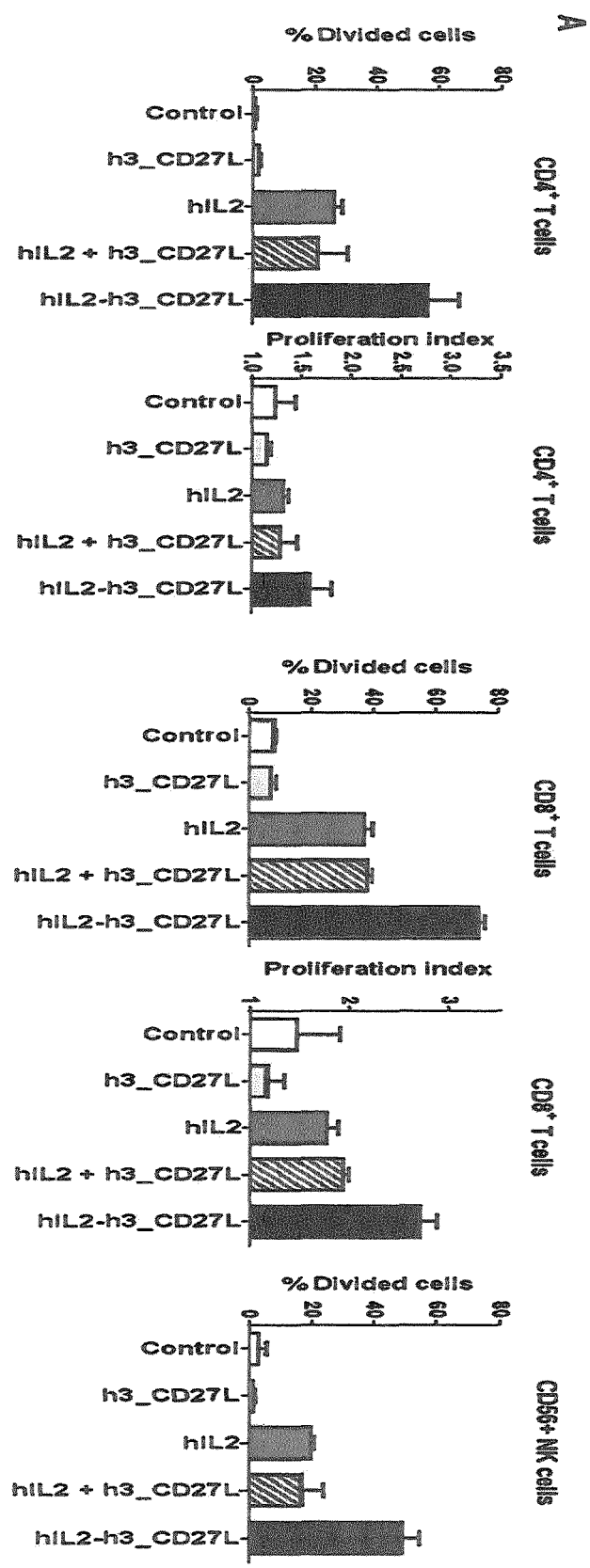
FIGS. 4A-4F show effects of IVT-RNA encoded hIL2-h3_TNFRL fusion proteins on T cell and NK cell proliferation. IVT-RNAs encoding fusion proteins consisting of human IL-2 and soluble TNFR ligand domains (h3_CD27L, h3_CD40L, h3_OX40L or h3_4-1BBL) were tested for their function on PBMC proliferation by an unspecific CFSE-proliferation assay. To this end, K562 cells were electroporated in a multi-well electroporation plate (96-well) with IVT-RNA encoding interleukins, extracellular domains of TNFR ligands or fusion proteins thereof. 20 pmol of RNA with reference to the corresponding encoded protein was used, unless otherwise specified. After 24 hours of incubation, supernatants were transferred to CFES-labeled PBMCs, which were sub-optimally activated by anti-CD3. CFSE-readout was performed after 5 days of incubation by flow cytometry; CD4$^+$ T cells, CD8$^+$ T cells and CD56$^+$ NK cells were stained with anti-human CD4-PE, CD8-PE-Cy7 and CD56-APC, respectively. Detailed analysis of proliferation based on peaks indicating cell divisions was made by the FlowJo software. By this means percentages of T cells that went into division, indicated by "% Divided cells", and average number of divisions of cells, which went into division, indicated by "proliferation index", were calculated (A to D). Representative histograms are shown in E and F. Effects of hIL2 fusion proteins in comparison to single cytokine encoded RNAs were analyzed for fusions with TNFR ligands h3_CD27L (A), h3_CD40L (B), h3_4-1BBL (C and E) and h3_OX40L (D and F).
Figure 4B:
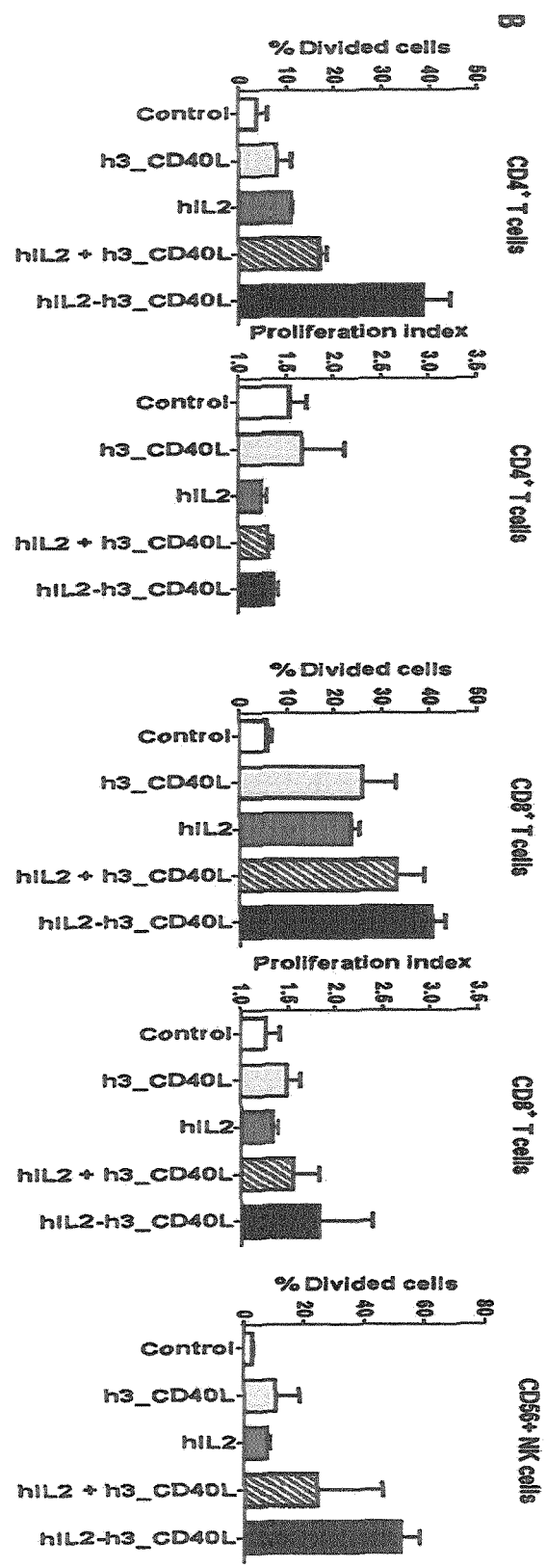
Figure 4C:
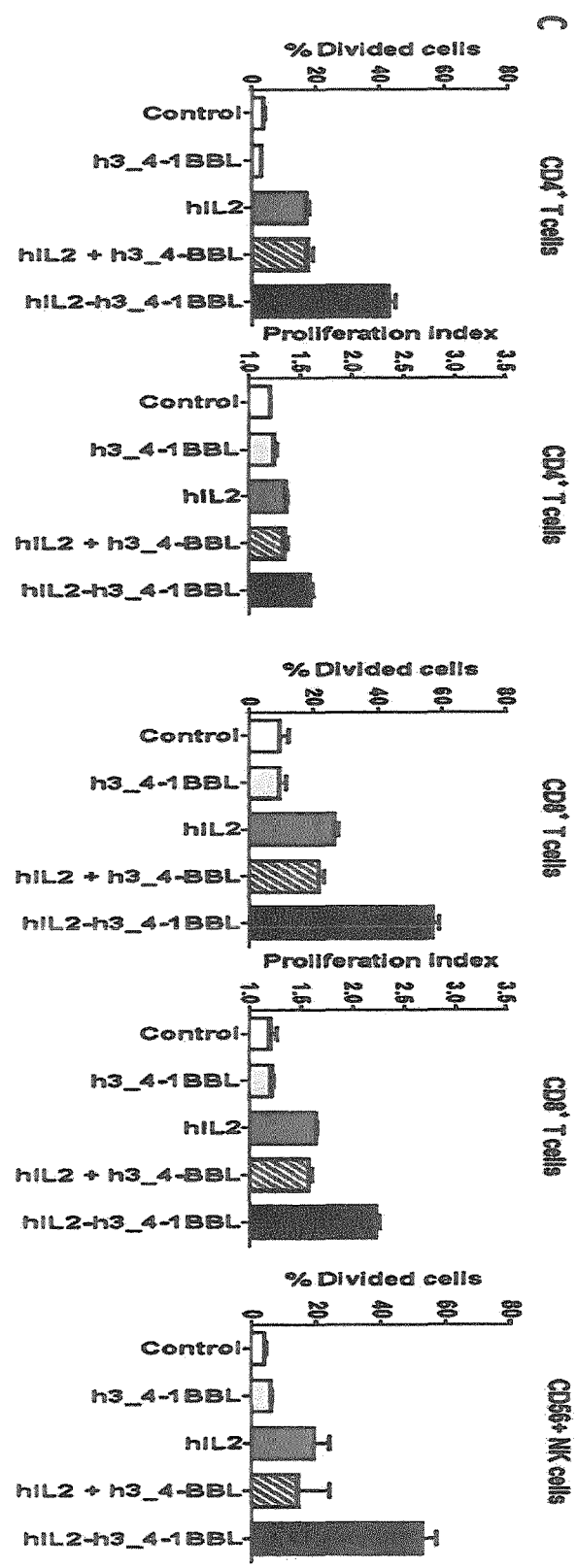
Figure 4D:
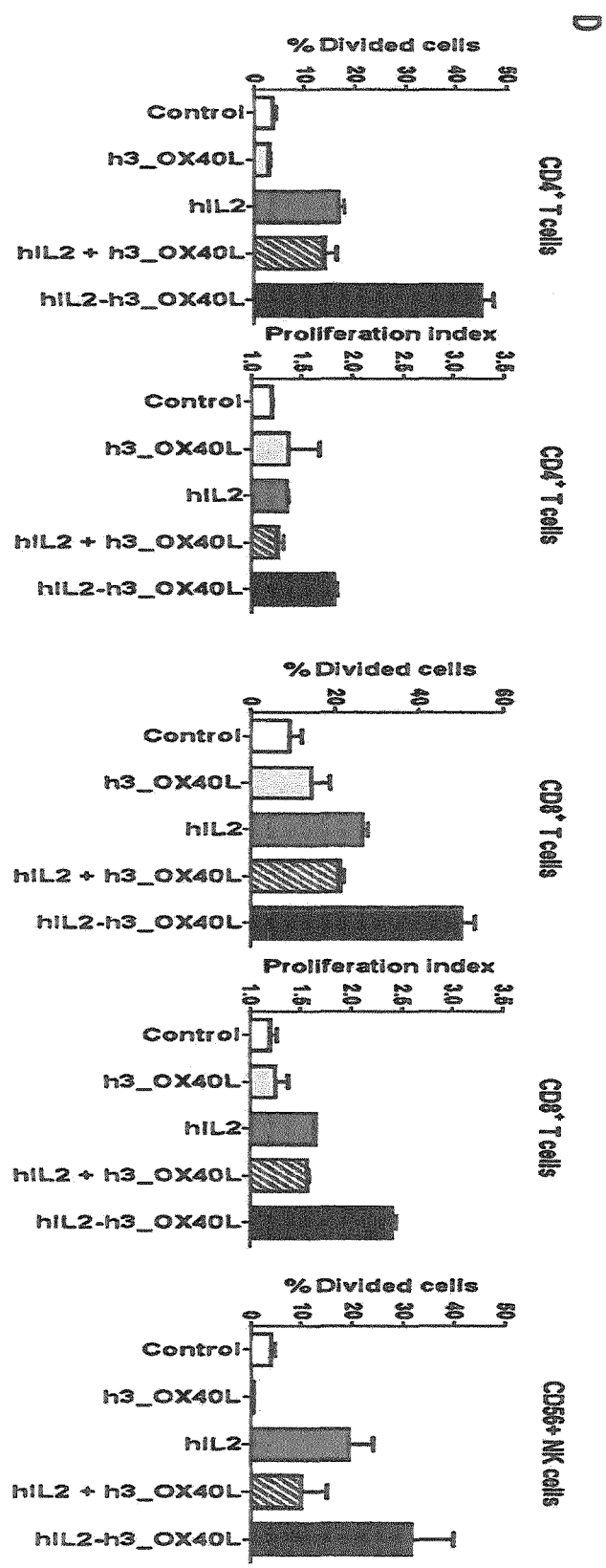
Figure 4:
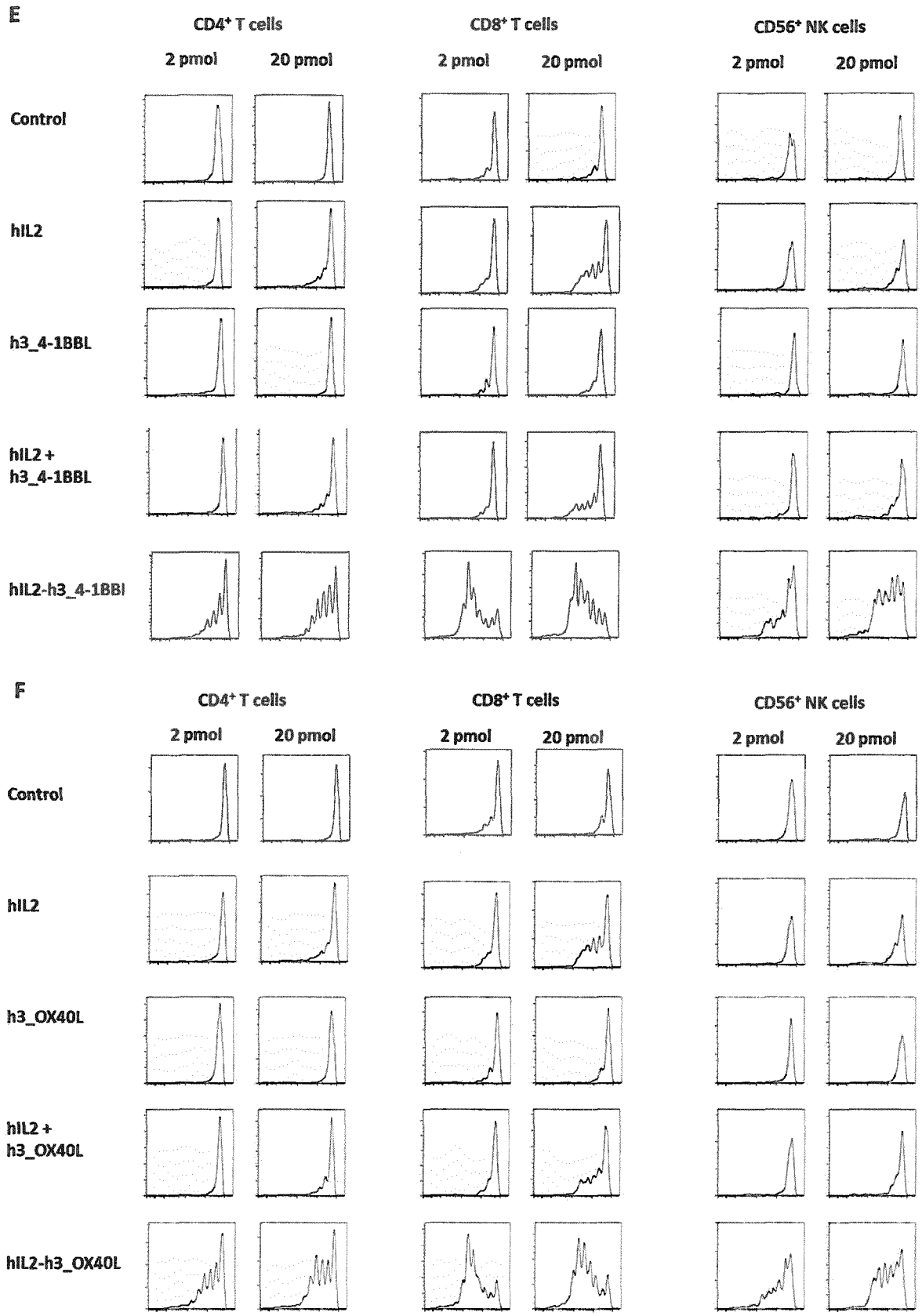

For the CFSE proliferation assay, PBMCs were obtained from blood donations from the Transfusionszentrale at the University Hospital in Mainz, Germany. PBMCs were stained with carboxyfluorescein succinimidyl ester (CFSE) according to the manufacturer's protocol (Invitrogen) and transferred to IMDM medium supplemented with 5% human AB serum. Anti-CD3 antibody (clone: UCHTI) was added to the cell suspension to a final concentration that had been determined in a PBMC donor-specific pre-test to result in a sub-optimal stimulation of the PBMCs. PBMCs were plated into 96-well plates at 50.000 cells in 150 µl medium per well. 50 µl of K562 supernatants (after 24 hours of incubation, see above) was added containing RNA encoded fusion proteins or single proteins, respectively. Incubation was carried out for 5 days and T cell proliferation was measured by flow cytometry and analyzed by the FlowJo software. CD4$^+$ T cells, CD8$^+$ T cells and CD56$^+$ NK cells cell suspension were distinguished by antibody staining.

hIL2 RNA alone induced moderate proliferation of CD4$^+$, CD8$^+$ T cells and NK cells. Mixture of hIL2 RNA with single RNAs encoding for soluble TNFR ligands mediated effects similar to hIL2 RNA alone. In contrast, RNAs encoding fusion proteins of hIL2 with a TNFR ligand strongly enhanced T cell and NK cell proliferation, or, more precisely, more T cells went into division and divided more often (FIGS. 4A-4F). Effects of hIL-2 fusion proteins were shown for fusions with all 4 tested TNF ligands, CD27L (FIG. 4 A), CD40L (FIG. 4 B), 4-1BBL (FIG. 4 C) and OX40L (FIG. 4 D). Representative histograms of cell divisions visualized by CFSE analysis are shown in FIG. 4 E (hIL2-h3_4-1BBL fusions) and FIG. 4 F (hIL2-h3_OX40L fusions).

Figure 5:
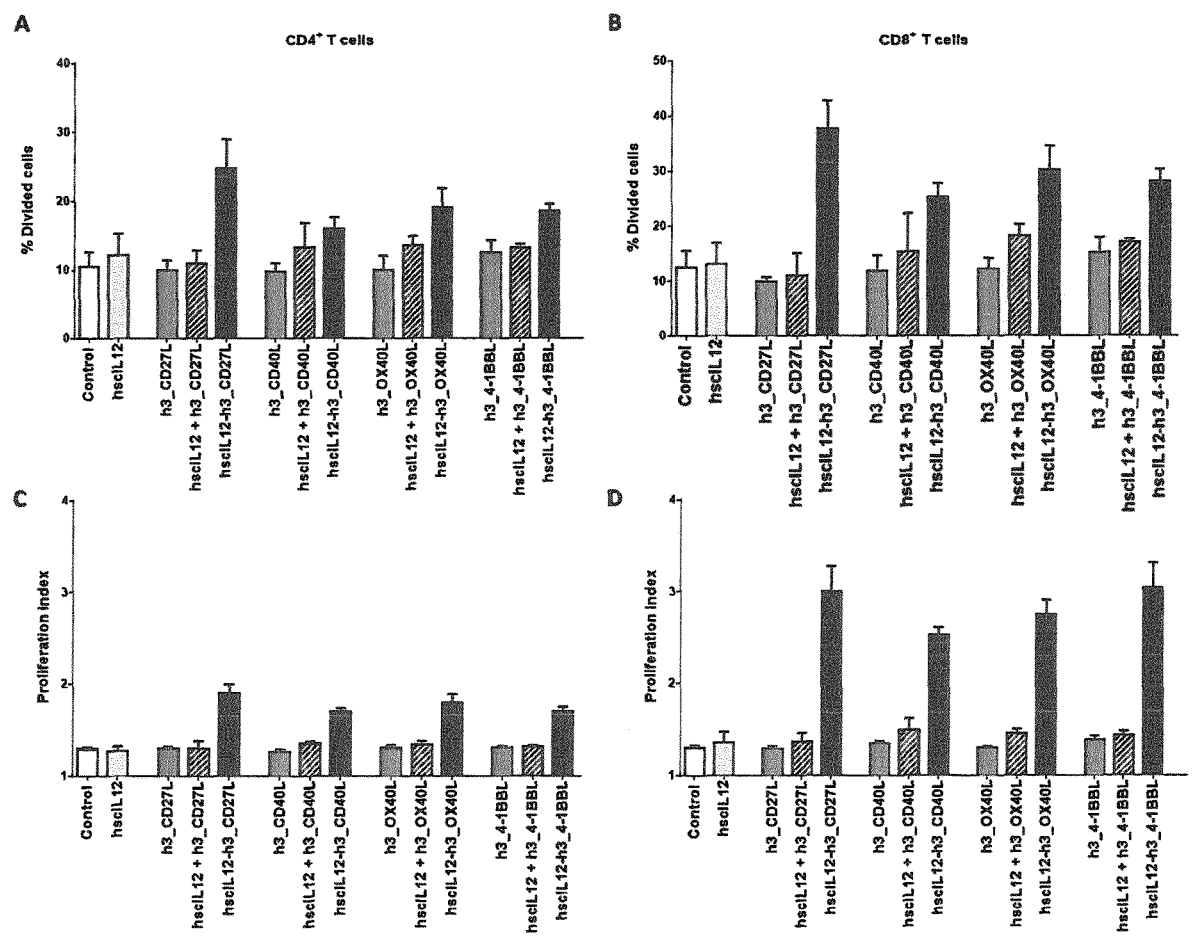
FIG. 5 shows effects of IVT-RNA encoded hscIL12-h3_TNFRL fusion proteins on T cell proliferation. Effects of hscIL12 fusion proteins in comparison to single cytokine encoding RNAs were analyzed for hscIl12 fusions with TNFR ligands h3_CD27L (A), h3_CD40L (B), h3_4-1BBL (C) and h3_OX40L (D). The assay was carried out as described in FIGS. 4A-4F (Example 4).

Example 5: Effects of IVT-RNA Encoded hscIL12-h3_TNFR Ligand Fusion Proteins on T Cell Proliferation IVT-RNAs encoding fusion protein consisting of human scIL12 and a soluble TNFR ligand domain (h3_CD27L, h3_CD40L, h3_OX40L or h3_4-1BBL) were tested for their effect on PBMC proliferation by the CFSE proliferation assay as descried above (Example 4). Superior effects of hscIL12 fusion proteins were shown for fusions with all 4 tested TNF ligands, h3_CD27L, h3_CD40L, h3_4-1BBL and h3_OX40L (FIG. 5). Strongest effects were observed for CD8$^+$ T cells (FIGS. 5B and D). hscIL12 fusion proteins particularly enhanced proliferation rates (numbers of cell divisions) (FIGS. 5C and D).

Example 6: Effects of IVT-RNA Encoded hIL2-h3 TNFR Ligand Fusion Proteins on Antigen-Specific T Cell Proliferation In order to analyze effects of cytokine fusion constructs on antigen-specific T cell proliferation, a CFSE CD8$^+$ T cell proliferation assay was set-up as follows. HLA-A2$^+$ PBMCs were obtained from blood donations from the Transfusionszentrale at the University Hospital in Mainz, Germany. Monocytes were isolated from PBMCs by magnetic-activated cell sorting (MACS) technology using anti-CD14

MicroBeads (Miltenyi); the peripheral blood lymphocytes (PBLs, CD14-fraction) were frozen for future T cell isolation. For differentiation into immature DC (iDC), monocytes were cultured for 4-5 days in RPMI GlutaMAX containing 5% Human AB-Serum (Gibco), sodium pyruvate (Gibco), non-essential amino acids, 100 IU/mL penicillin, and 100 µg/mL streptomycin, 1000 IU/mL granulocyte-macrophage colony-stimulating factor and 1000 IU/mL IL-4 (both from Miltenyi). Half of the medium was replaced with fresh medium once during these 4-5 days. iDCs were harvested and washed once in X-Vivo15 medium prior to electroporation and re-suspended to 1×10⁶-5×10⁶ cells/250 µl in X-Vivo15 again and transferred to an electroporation cuvette. RNA encoding the antigen claudin-6 was added, and then the cell suspension was mixed. iDC electroporation was performed in 250 µl X-Vivo15 in a 4 mm electroporation cuvette using the BTX ECM® 830 Electroporation System device (300 V, 1×12 ms pulse). Immediately after electroporation, cells were transferred into a 6-well plate containing IMDM medium supplemented with 5% human AB serum and rested overnight in the incubator.

In order to generate supernatants containing human interleukin TNFR ligand fusion proteins, K562 multi-electroporation was performed as described above. CD8⁺ T cells were separated by MACS technology using anti-CD8 MicroBeads (Miitenyi) from remaining HLA-A2⁺ peripheral blood lymphocytes, which were frozen after CD14⁺ MACS isolation. CD8⁺ T cells were washed once in X-vivo 15 medium and re-suspended to a final concentration of 10-15× 10⁶ cells/250 µl in X-Vivo15 again. 10-15×10⁶ CD8⁺ T cells were electroporated in 250 µl medium with 10 µg of IVT-RNA encoding the alpha-chain plus 10 µg of IVT-RNA encoding the beta-chain of a claudin-6-TCR (restricted to HLA-A2⁺). Electroporation was performed in 250 µl X-Vivo15 in a 4 mm electroporation cuvette using the BTX device (500 V, 1×3 ms pulse). Immediately after electroporation, cells were transferred into fresh IMDM medium supplemented with 5% human AB serum and rested for at least 1 hour in the incubator. Then, T cells were stained with CFSE and rested overnight in the incubator.

One day after electroporation, a total of 5.000 DCs electroporated with claudin-6 RNA and 50.000 T cells electroporated with RNA encoding CLD6-TCR were mixed in a volume of 100 µl of RPMI 1640 GlutaMAX supplemented with 5% human AB serum 100 IU/mL penicillin, and 100 mg/mL streptomycin per well of a 96-well round bottom plate. 50 µl of K562 supernatants containing secreted interleukin TNFR ligand fusions (24 hours of incubation after multi-well electroporation) were added per well to the DC:T cell suspension. Incubation was carried out, and T cell proliferation was measured after 5 days of incubation by flow cytometry and analyzed by the FlowJo software.

Figure 6:
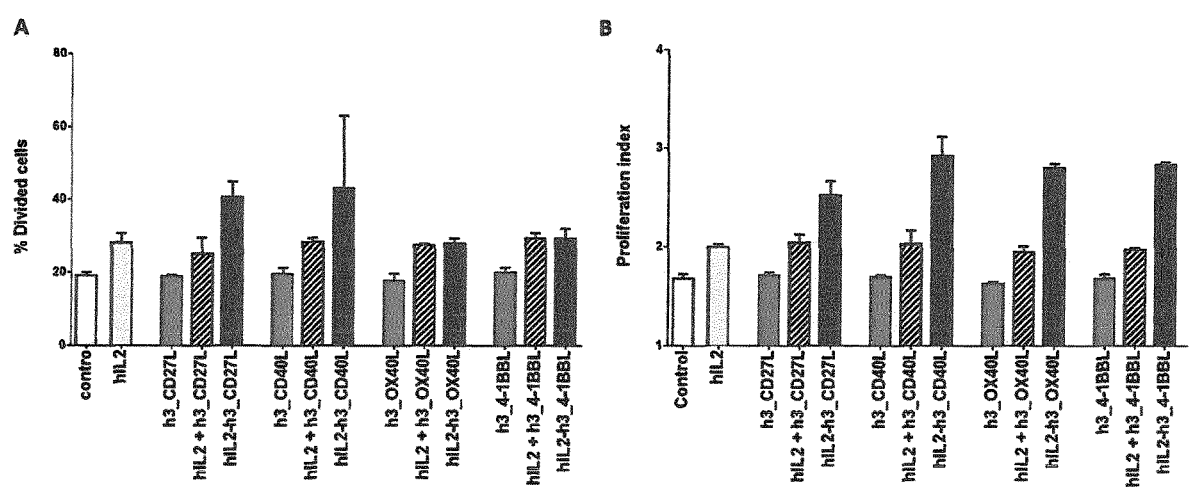
FIG. 6 shows effects of IVT-RNA encoded hIL2-h3_TNFRL fusion proteins on antigen-specific T cell proliferation. iDCs were electroporated with claudin-6 IVT-RNA. CD8$^+$ T cells (HLA-A2$^+$ donor) were electroporated with IVT-RNA coding for a claudin-6-specific CD8$^+$ T cell receptor and afterwards stained with CFSE. One day after electroporation, iDCs and CD8$^+$ T cells were co-cultured in a ratio of 1:10 for 4 days; supernatants from electroporated K562 cells after 24 hours of incubation were added to the co-cultures. K562 cells had been electroporated in a multi-well electroporation plate (96-well) with WT-RNA (20 pmol referring to translated proteins) encoding interleukins, extracellular domains of TNFR ligands or fusion proteins thereof as indicated. CD8$^+$ T cell proliferation was analyzed by FACS. Detailed analysis of proliferation based on peaks indicating cell divisions was made by the FlowJo software. By this means percentages of T cells that went into division, indicated by "% Divided cells", and average number of divisions of cells, which went into division, indicated by "proliferation index", was calculated, both shown in (A) and (B), respectively. hIL2-h3_TNFRL fusion proteins enhanced proliferation to a higher extent than a mixture of corresponding single RNAs. More precisely, all hIL2-h3_TNFRL fusion resulted in higher number of cell divisions (B) and, additionally, upon application of hIL2-h3_CD27L and hIL2-h3_CD40L fusion constructs, more cells went into division (A).

IVT-RNAs encoding fusion protein consisting of human IL2 and a soluble TNF ligand domain (CD27L, CD40L, OX40L or 4-1BBL) were tested for their effect on CD8⁺ T cell proliferation in an antigen-specific setting (FIG. 6). IL2 RNA alone induced moderate proliferation of CD8⁺ T cells. Mixture of IL2 RNA with single RNAs encoding for soluble TNF ligands mediated effects similar to IL2 RNA alone. In contrast, RNAs encoding fusion proteins of IL2 with a TNFR ligand strongly enhanced T cell proliferation. More detailed analysis revealed that all 4 hIL2 fusion proteins enhanced the proliferation index (numbers of cell divisions) (FIG. 6B). In addition, hIL-2-CD27L and hIL2-CD40L fusions enhanced percentage of divided cells (cells that went into division) (FIG. 6A).

The invention claimed is:

1. An RNA molecule encoding a fusion protein, wherein the fusion protein comprises a molecule/structure having the general formula $$N'\text{-}A\text{-}L_4\text{-}A\text{-}L_4\text{-}A\text{-}L\text{-}B\text{---}C' \quad \text{(Formula I) or}$$

$$N'\text{---}B\text{-}L\text{-}A\text{-}L_4\text{-}A\text{-}L_4\text{-}A\text{-}C', \quad \text{(Formula II)},$$

wherein A comprises an extracellular domain of a ligand of the tumor necrosis factor (TNF) superfamily or a functional variant thereof, said extracellular domain comprises at least a functional TNF homology domain (THD), and said variant of the extracellular domain has at least 95% sequence identity to the extracellular domain and is able to bind to a member of the TNF superfamily upon trimerization, B comprises an interleukin, or a functional fragment or a functional variant of the functional fragment, said variant has at least 95% sequence identity to the functional fragment of the interleukin and is able to bind to a receptor of the interleukin, and L comprises a peptide linker, and $L_4$ is, at each occurrence, independently a covalent bond or a peptide linker.

2. The RNA molecule according to claim 1, wherein L further comprises a multimerization domain allowing the multimerization of the fusion protein.

3. The RNA molecule according to claim 2, wherein the multimerization domain is a dimerization domain and is selected from the group consisting of an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an Fc domain, and an uteroglobin dimerization domain.

4. The RNA molecule according to claim 2, wherein, upon expression of the fusion protein, the fusion protein is present as a multimeric complex.

5. The RNA molecule according to claim 1, wherein the ligand is selected from the group consisting of CD40 ligand (CD40L), CD27 ligand (CD27L), 4-1BB ligand (4-1BBL), OX40 ligand (OX40L), A proliferation-inducing ligand (APRIL), CD30 ligand (CD30L), Ectodysplasin-A1 (EDA-A1), Ectodysplasin-A2 (EDA-A2), fas ligand (FasL), GITR ligand (GITRL), LIGHT, Lymphotoxin-alpha (LT-alpha), TL1A, tumor necrosis factor alpha (TNF-alpha), TNF-related apoptosis-inducing ligand (TRAIL), receptor activator of NF-kB ligant (RANKL), and TWEAK.

6. The RNA molecule according to claim 5, wherein the extracellular domain of CD40L comprises or consists of amino acid residues 51 to 261 or 116 to 261 of SEQ ID NO: 1, the extracellular domain of CD27L comprises or consists of amino acid residues 52 to 193 of SEQ ID NO: 2, the extracellular domain of 4-1BBL comprises or consists of amino acid residues 71 to 254 of SEQ ID NO: 3, and/or the extracellular domain of OX40L comprises or consists of amino acid residues 51 to 183 of SEQ ID NO: 4.

7. The RNA molecule according to claim 1, wherein the interleukin is selected from the group consisting of IL2, IL12, IL21, IL27, IL1-alpha, IL1-beta, IL7, IL15, IL18, IL9, IL23, IL4, IL6, IL10, IL31 and IL33.

8. The RNA molecule according to claim 7, wherein the interleukin is a heterodimeric interleukin being present as a single polypeptide.

9. The RNA molecule according to claim 1, wherein the fusion protein further comprises at least one label or tag allowing the detection and/or isolation of the fusion protein.

10. The RNA molecule according to claim 1, wherein the fusion protein enhances proliferation of natural killer (NK) cells and/or T cells.

11. The RNA molecule according to claim 1, which is an in vitro-transcribed (IVT) RNA molecule.

12. The RNA molecule according to claim 1, wherein L further comprises a dimerization domain allowing the dimerization of the fusion protein.

13. The RNA molecule according to claim 2, wherein, upon expression of the fusion protein, the fusion protein is present as a dimeric complex.

14. The RNA molecule according to claim 5, wherein the ligand is selected from the group consisting of CD40L, CD27L, 4-1BBL, and OX40L.

15. The RNA molecule according to claim 10, wherein the fusion protein enhances proliferation of $CD8^+$ T cells.

16. The RNA molecule according to claim 1, wherein, upon expression of the fusion protein, the three extracellular domains or functional variants thereof, form a homotrimer capable of binding to a receptor of the ligand.

17. A cell transformed or transfected with an RNA molecule according to claim 1.

18. A non-human organism transformed or transfected with an RNA molecule according to claim 1.

19. A pharmaceutical composition comprising (i) as an active agent, an RNA molecule according to claim 1 and (ii) a pharmaceutically acceptable carrier and/or excipient.

20. A pharmaceutical composition comprising (i) as an active agent, a cell according to claim 17 and (ii) a pharmaceutically acceptable carrier and/or excipient.

21. A kit comprising an RNA molecule according to claim 1.

22. A kit comprising a cell according to claim 17.

23. A kit comprising a pharmaceutical composition of claim 19.

24. A kit comprising a pharmaceutical composition of claim 20.

25. A method comprising administering an effective amount of an RNA molecule according to claim 1 to a subject in need thereof.

26. A method comprising administering an effective amount of a cell according to claim 17 to a subject in need thereof.

27. A method comprising administering an effective amount of a pharmaceutical composition according to claim 19 to a subject in need thereof.

28. A method comprising administering an effective amount of a pharmaceutical composition according to claim 20 to a subject in need thereof.

* * * * *